(12) United States Patent
Chavez et al.

(10) Patent No.: US 11,566,009 B1
(45) Date of Patent: Jan. 31, 2023

(54) ENERGETIC COMPOUND EMBODIMENTS AND METHODS OF MAKING AND USING THE SAME

(71) Applicants: Triad National Security, LLC, Los Alamos, NM (US); The United States of America, as represented by the Secretary of the Army, Washington, DC (US)

(72) Inventors: David Chavez, Los Alamos, NM (US); Jesse Sabatini, Bel Air, MD (US); Pablo Guzmán, Bel Air, MD (US); Leah Wingard, Landenberg, PA (US); Eric Johnson, Millington, MD (US)

(73) Assignees: Triad National Security, LLC, Los Alamos, NM (US); The United States of America as represented by the Secretary of the Army, Washington, DC (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 16/875,544

(22) Filed: May 15, 2020

Related U.S. Application Data

(60) Provisional application No. 62/849,676, filed on May 17, 2019.

(51) Int. Cl.
*C07D 271/06* (2006.01)
*C06B 25/34* (2006.01)

(52) U.S. Cl.
CPC ............ *C07D 271/06* (2013.01); *C06B 25/34* (2013.01)

(58) Field of Classification Search
CPC .............................. C07D 271/06; C06B 25/34
See application file for complete search history.

(56) References Cited

U.S. PATENT DOCUMENTS

| | | | |
|---|---|---|---|
| 2,543,472 A | 2/1951 | Senkus | |
| 6,342,589 B1 | 1/2002 | Hiskey et al. | |
| 8,324,421 B2 | 12/2012 | Chavez et al. | |
| 9,994,532 B1 * | 6/2018 | Sabatini | ................ C06B 45/105 |
| 2019/0062287 A1 | 2/2019 | Sabatini et al. | |

OTHER PUBLICATIONS

STN Registry Entry for CAS RN 2104547-94-4, Accessed Apr. 10, 2021, Entered STN Jul. 28, 2017.*
Johnson et al., Org. Process Res. Dev. 2018, 22, 736-740.*
Sausa et al., J. Phys. Chem. A, 2018, 122, 46, 9043-9053.*
CAS RN 141737-47-5, STN Registry Database, Entered STN Jun. 12, 1992, Accessed Dec. 17, 2021.*

* cited by examiner

*Primary Examiner* — Alicia L Otton
(74) *Attorney, Agent, or Firm* — Klarquist Sparkman, LLP

(57) ABSTRACT

Disclosed herein are embodiments of an energetic compound and methods of making and using the same. Energetic compound embodiments disclosed herein exhibit physical and chemical properties that facilitate their use in various applications, such as high energy propellant plasticizers, melt-castable explosives, and the like. Efficient and safe method embodiments for making the disclosed energetic compound embodiments are described herein.

13 Claims, 13 Drawing Sheets

US 11,566,009 B1

ENERGETIC COMPOUND EMBODIMENTS AND METHODS OF MAKING AND USING THE SAME

CROSS-REFERENCE TO RELATED APPLICATION

This application claims the benefit of the earlier filing date of U.S. Provisional Application No. 62/849,676, filed on May 17, 2019, the entirety of which is incorporated herein by reference.

ACKNOWLEDGMENT OF GOVERNMENT SUPPORT

This invention was made with government support under Contract No. 89233218CN000001 awarded by the U.S. Department of Energy/National Nuclear Security Administration. The government has certain rights in the invention.

FIELD

Disclosed herein are embodiments of an energetic compound and methods of making and using the same.

BACKGROUND

The development of high-energy-density materials (HEDMs) with excellent performance and reasonable sensitivity is an overarching goal in the field of energetic materials. High-energy-density melt-castable explosives are a particularly challenging area in which to attain this goal. Melt-cast explosives are sought because they allow for scalable and efficient manufacturing processes. However, these materials must also possess specific unique properties, which significantly narrows the range of new target materials that can be pursued. There is a need in the art for new materials that can be used as energetic materials and/or plasticizer ingredients and methods of making such materials that are safe and scalable.

SUMMARY

Disclosed herein are new embodiments of an energetic compound. Formulas and structures for compound embodiments are provided herein. Also disclosed are embodiments of a method for making the compound embodiments of the present disclosure. In some embodiments, the method comprises exposing a bis-oxadiazole product to a nitrating agent to provide a bis-oxadiazole dinitrate. In some embodiments, the method further comprises making the bis-oxadiazole product by combining a diaminoglyoxime product with a carbonyl-containing reagent to form a reaction mixture and heating the reaction mixture at a temperature above room temperature. In yet additional embodiments, the method can comprise making the diaminoglyoxime product by combining a di-aldehyde precursor compound with a hydroxylamine.

Also disclosed herein are embodiments of a method of using compound embodiments disclosed herein wherein the method comprises making a melt-castable explosive composition and/or a propellant plasticizer composition with the compound.

The foregoing and other objects and features of the present disclosure will become more apparent from the following detailed description, which proceeds with reference to the accompanying figures.

DETAILED DESCRIPTION

I. Overview of Terms

Figure 1:
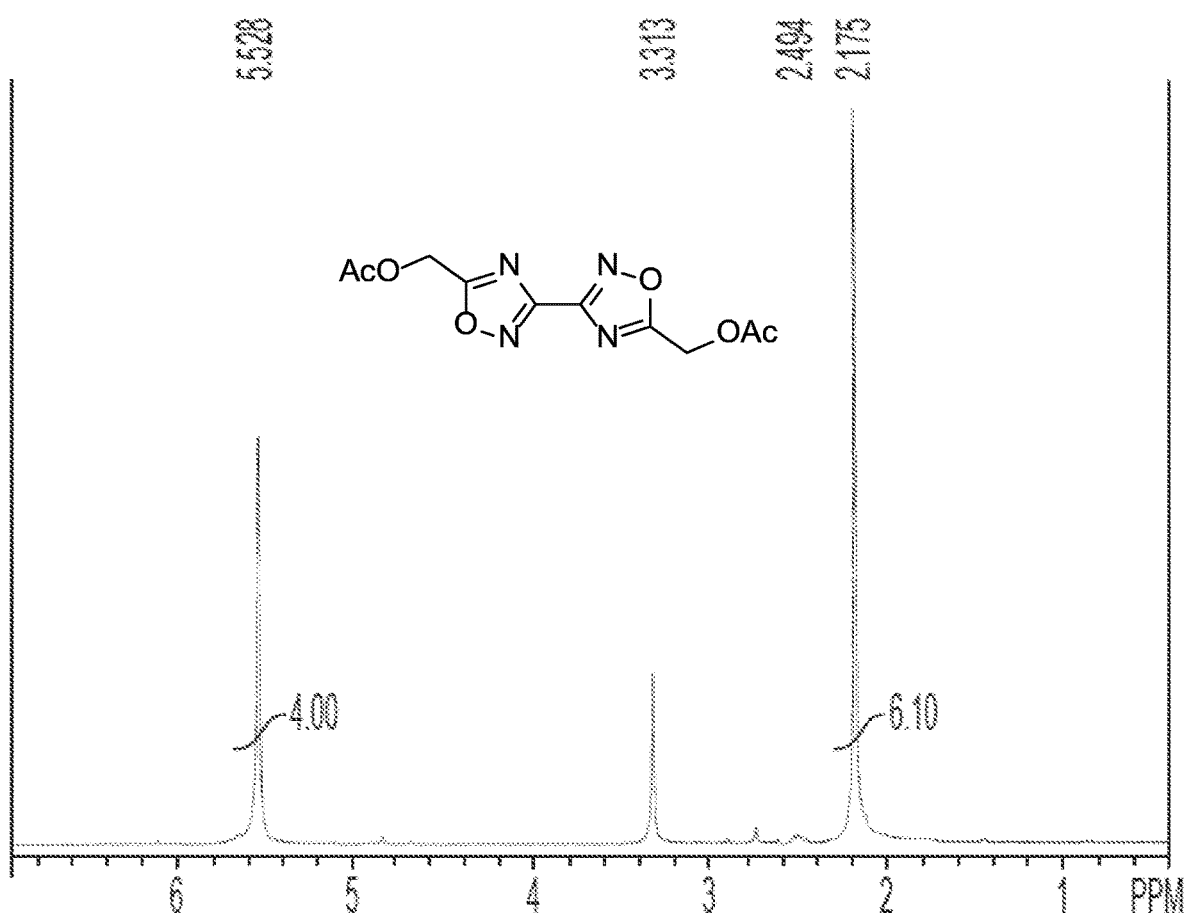
FIG. 1 is a $^1$H nuclear magnetic resonance (NMR) spectrum for an energetic compound intermediate, [3,3'-bis(1,2,4-oxadiazole)]-5,5'-diylbis(methylene).
Figure 2:
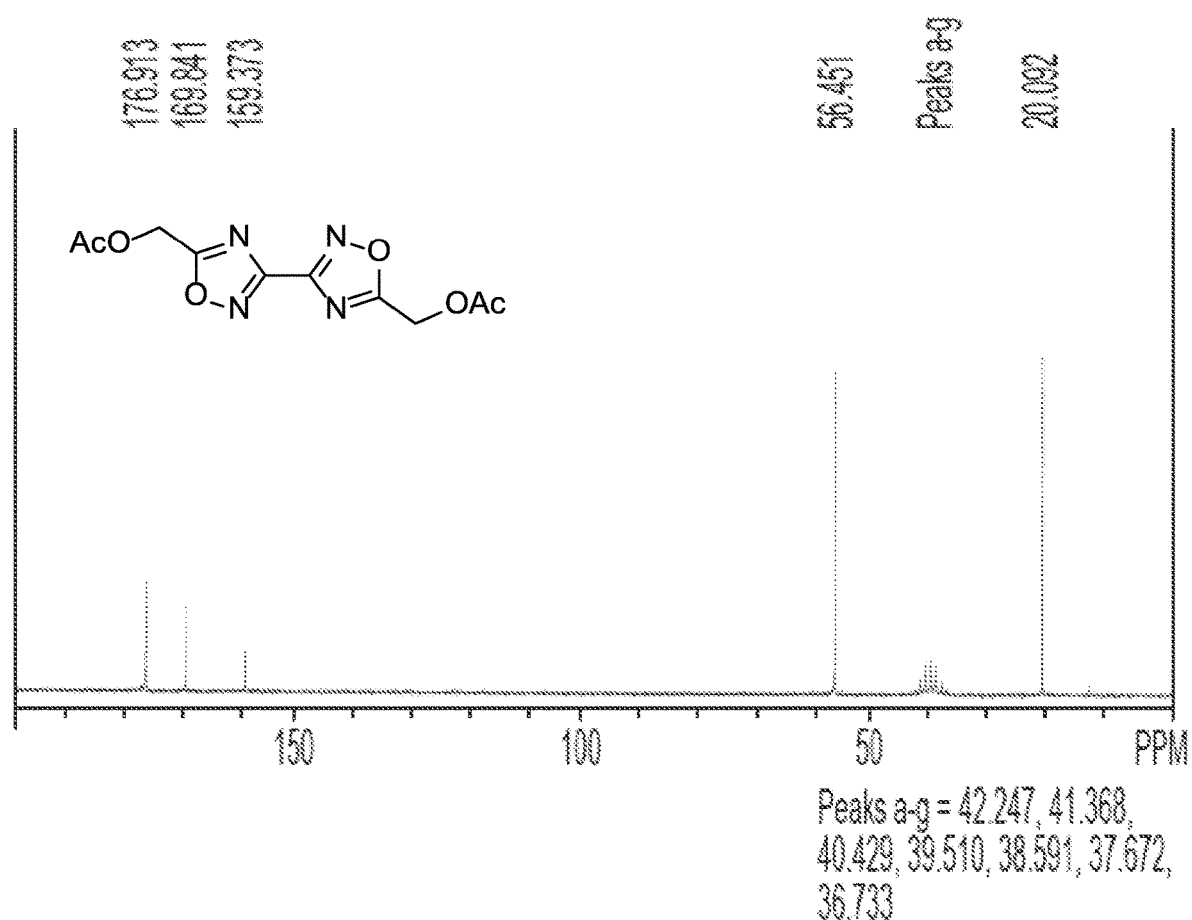
FIG. 2 is a $^{13}$C NMR spectrum for [3,3'-bis(1,2,4-oxadiazole)]-5,5'-diylbis(methylene).
Figure 3:
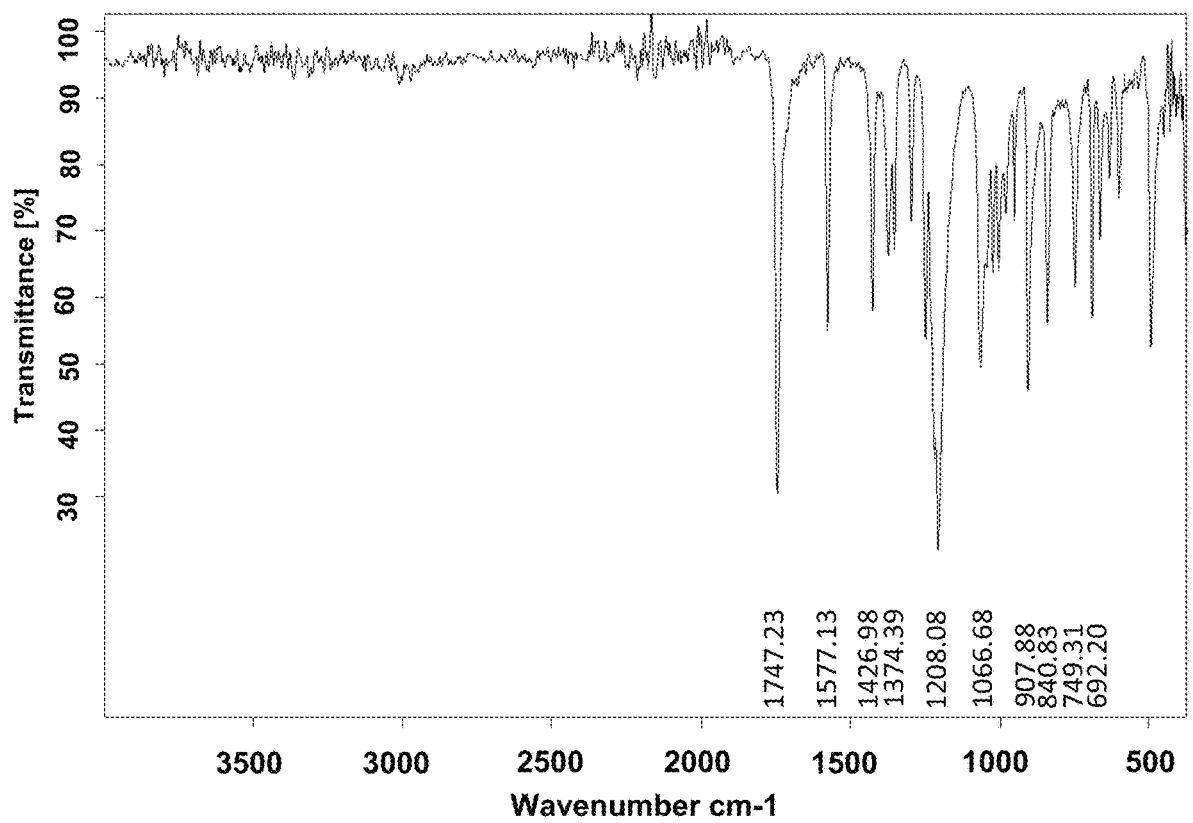
FIG. 3 is an infrared (IR) spectrum for [3,3'-bis(1,2,4-oxadiazole)]-5,5'-diylbis(methylene).
Figure 4:
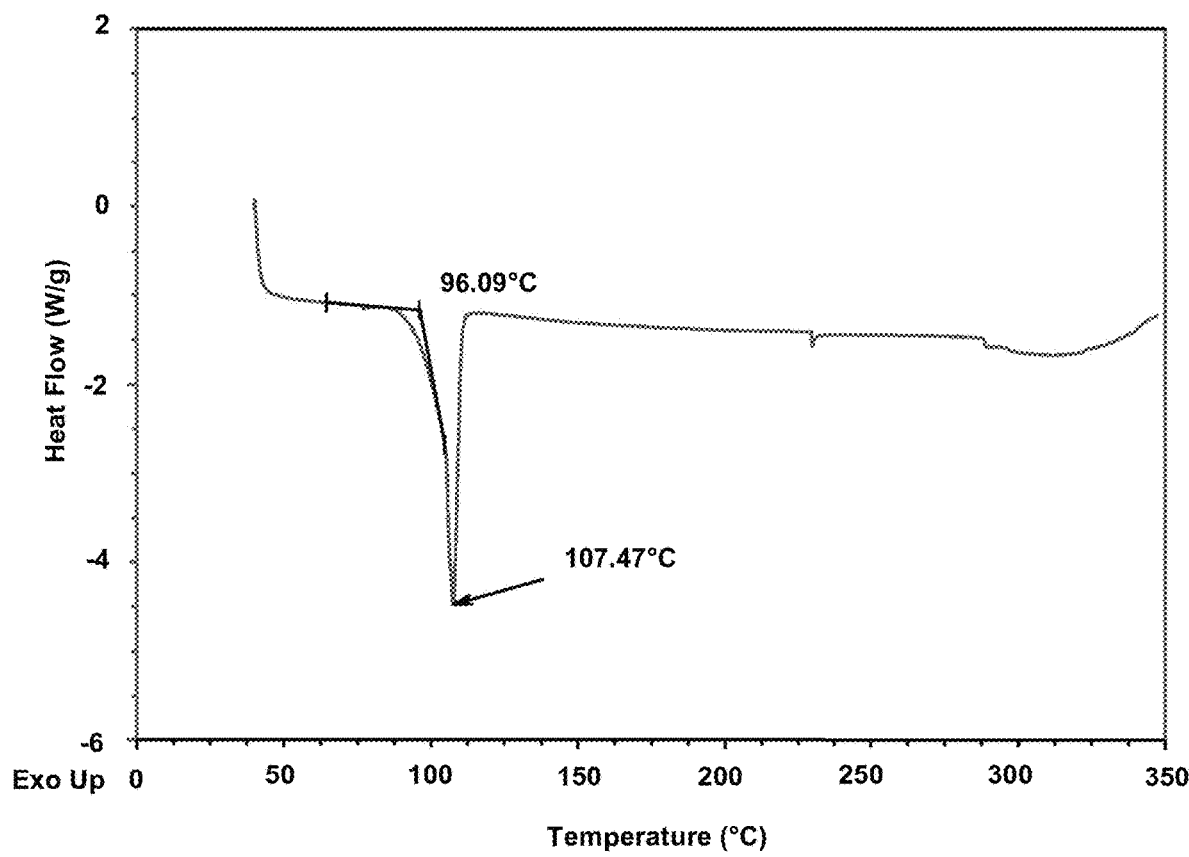
FIG. 4 is a differential scanning calorimetry (DSC) spectrum for [3,3'-bis(1,2,4-oxadiazole)]-5,5'-diylbis(methylene).
Figure 5:
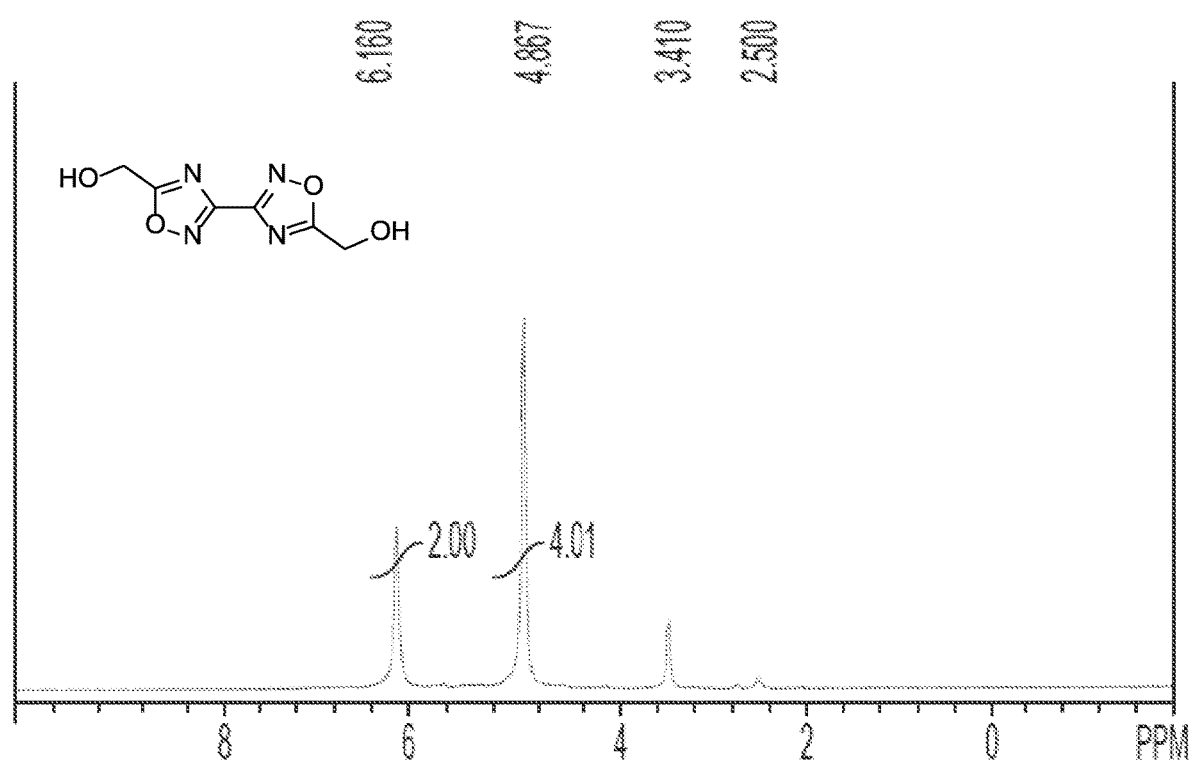
FIG. 5 is a $^1$H nuclear magnetic resonance (NMR) spectrum for an energetic compound intermediate, [3,3'-bis(1,2,4-oxadiazole)]-5,5'-diyldimethanol.
Figure 6:
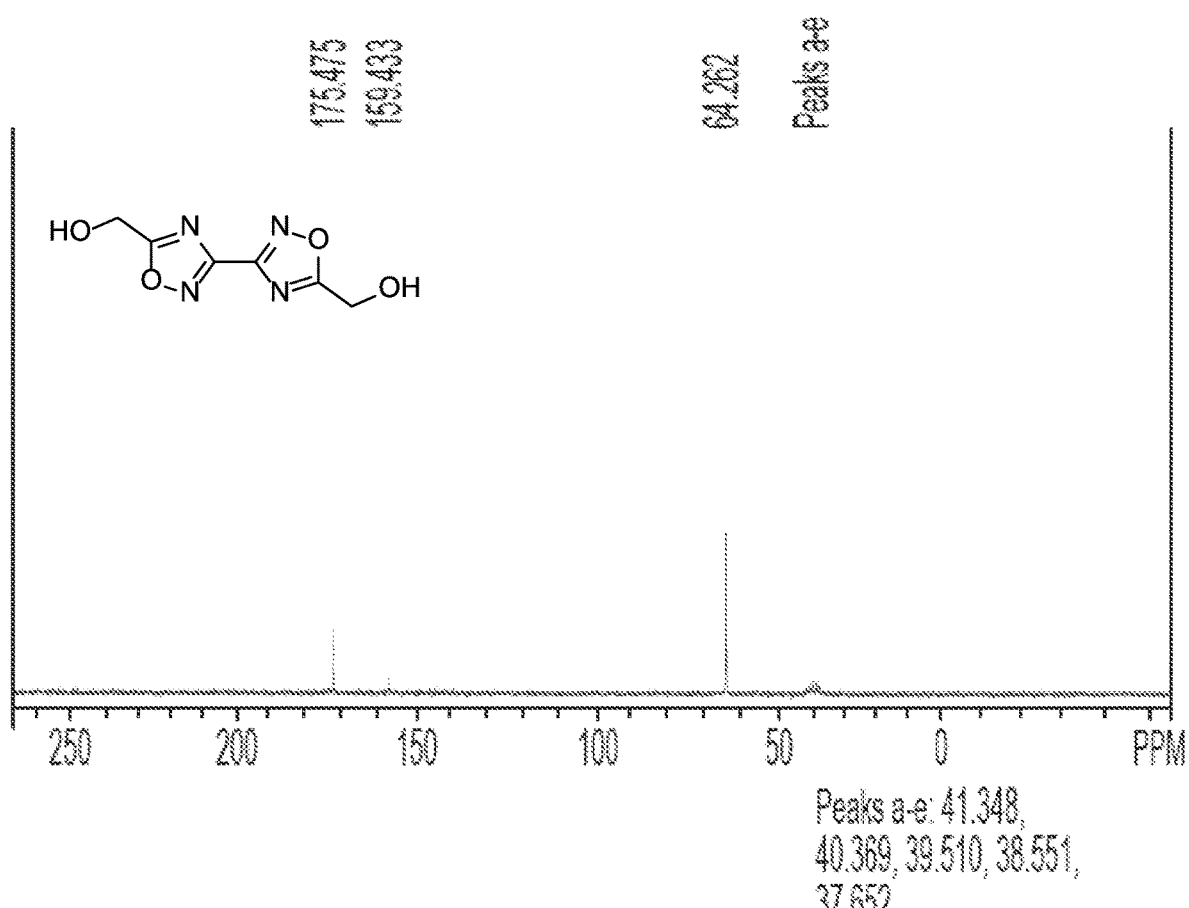
FIG. 6 is a $^{13}$C NMR spectrum for [3,3'-bis(1,2,4-oxadiazole)]-5,5'-diyldimethanol.
Figure 7:
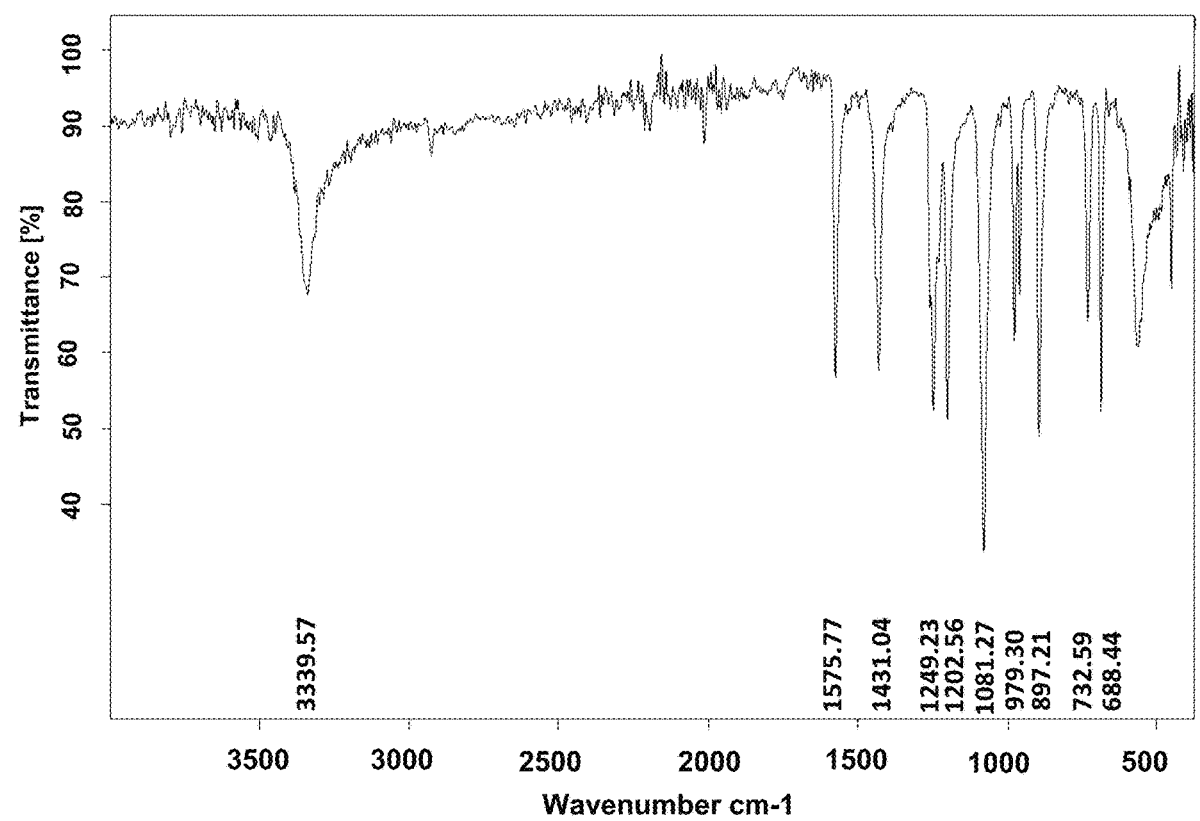
FIG. 7 is an infrared (IR) spectrum for [3,3'-bis(1,2,4-oxadiazole)]-5,5'-diyldimethanol.
Figure 8:
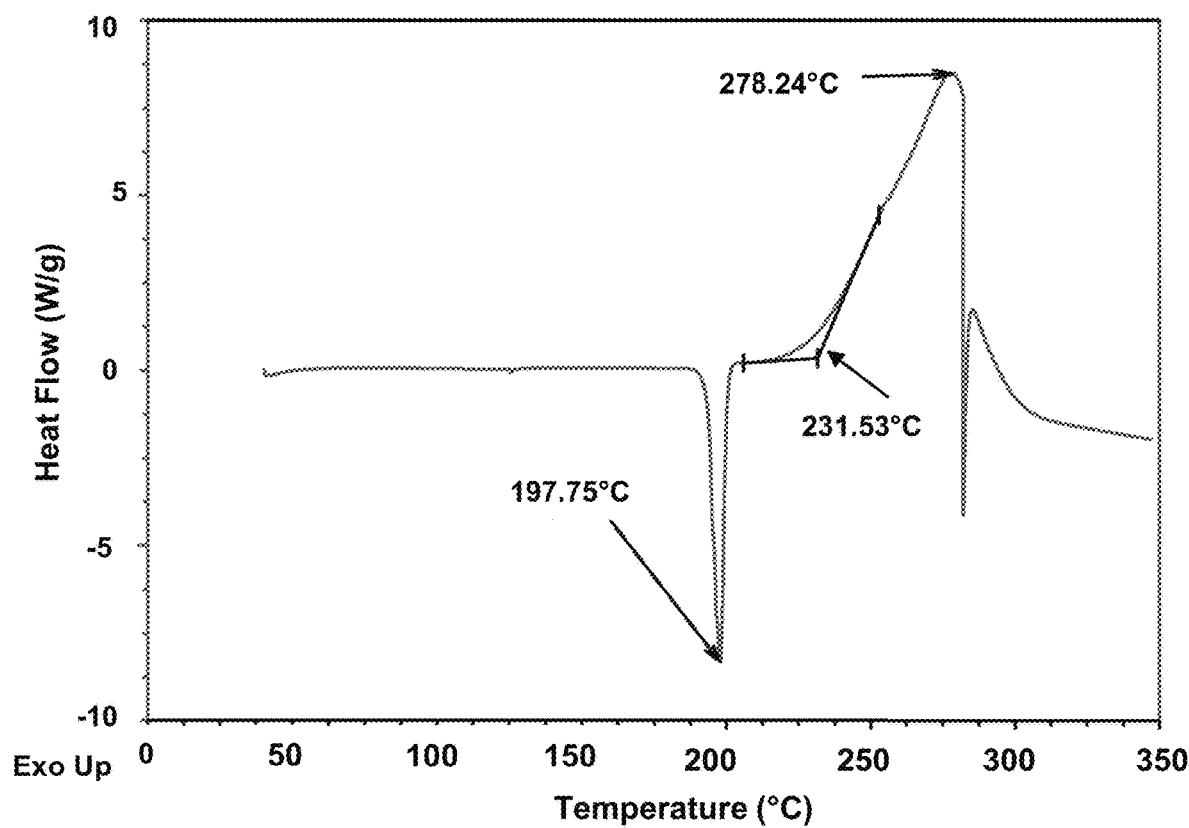
FIG. 8 is a differential scanning calorimetry (DSC) spectrum for [3,3'-bis(1,2,4-oxadiazole)]-5,5'-diyldimethanol.
Figure 9:
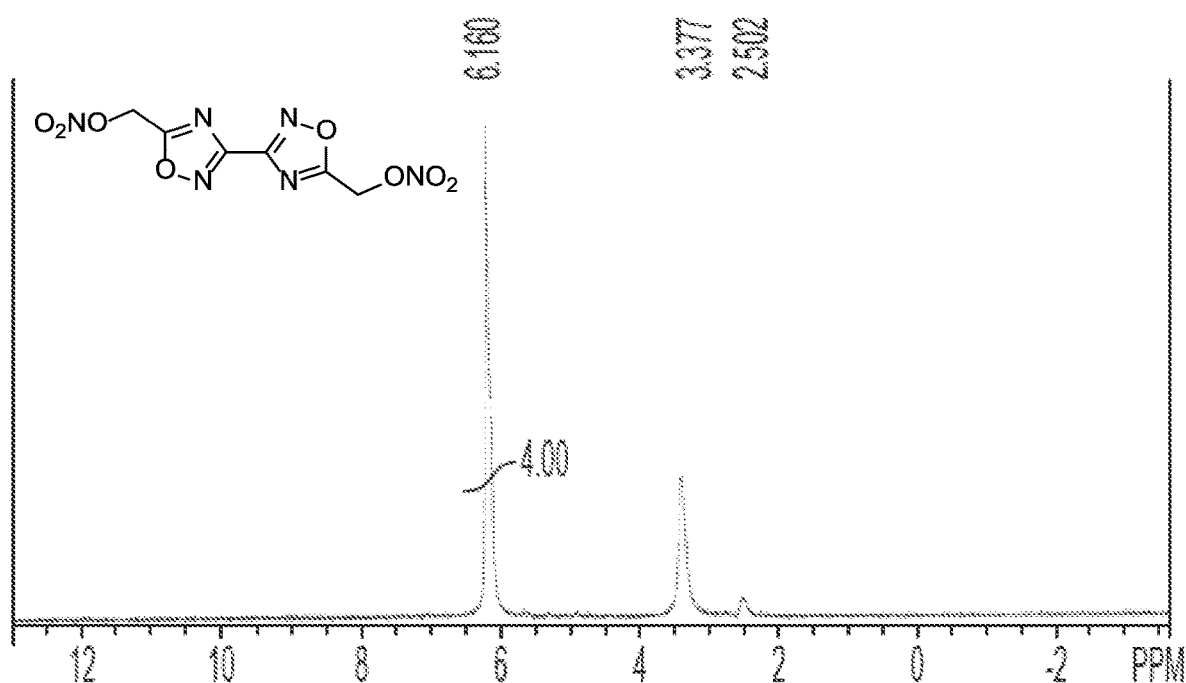
FIG. 9 is a $^1$H nuclear magnetic resonance (NMR) spectrum for an energetic compound embodiment, [3,3'-bis(1,2,4-oxadiazole)]-5,5'-diylbis(methylene) dinitrate.
Figure 10:
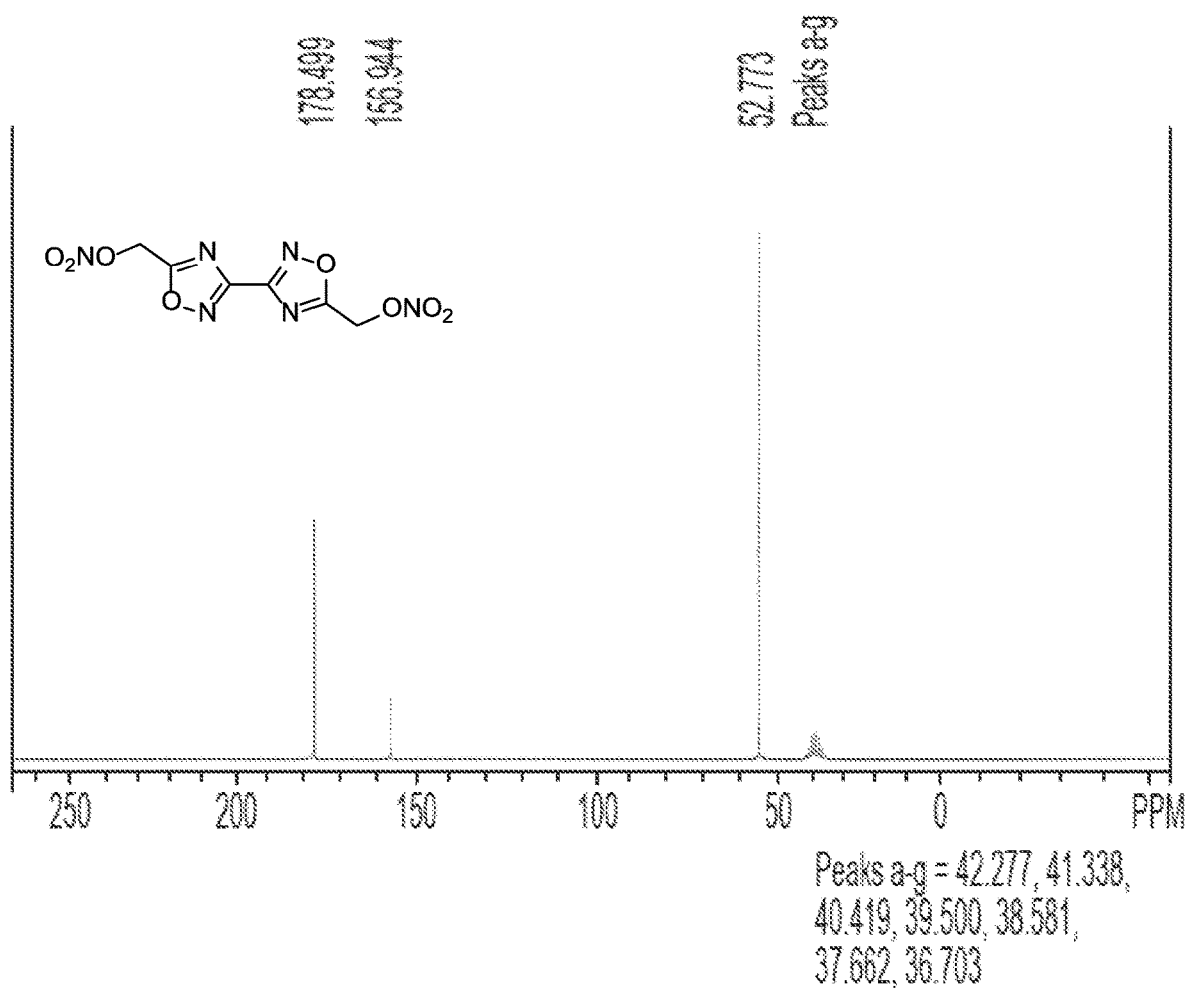
FIG. 10 is a $^{13}$C NMR spectrum for [3,3'-bis(1,2,4-oxadiazole)]-5,5'-diylbis(methylene) dinitrate.
Figure 11:
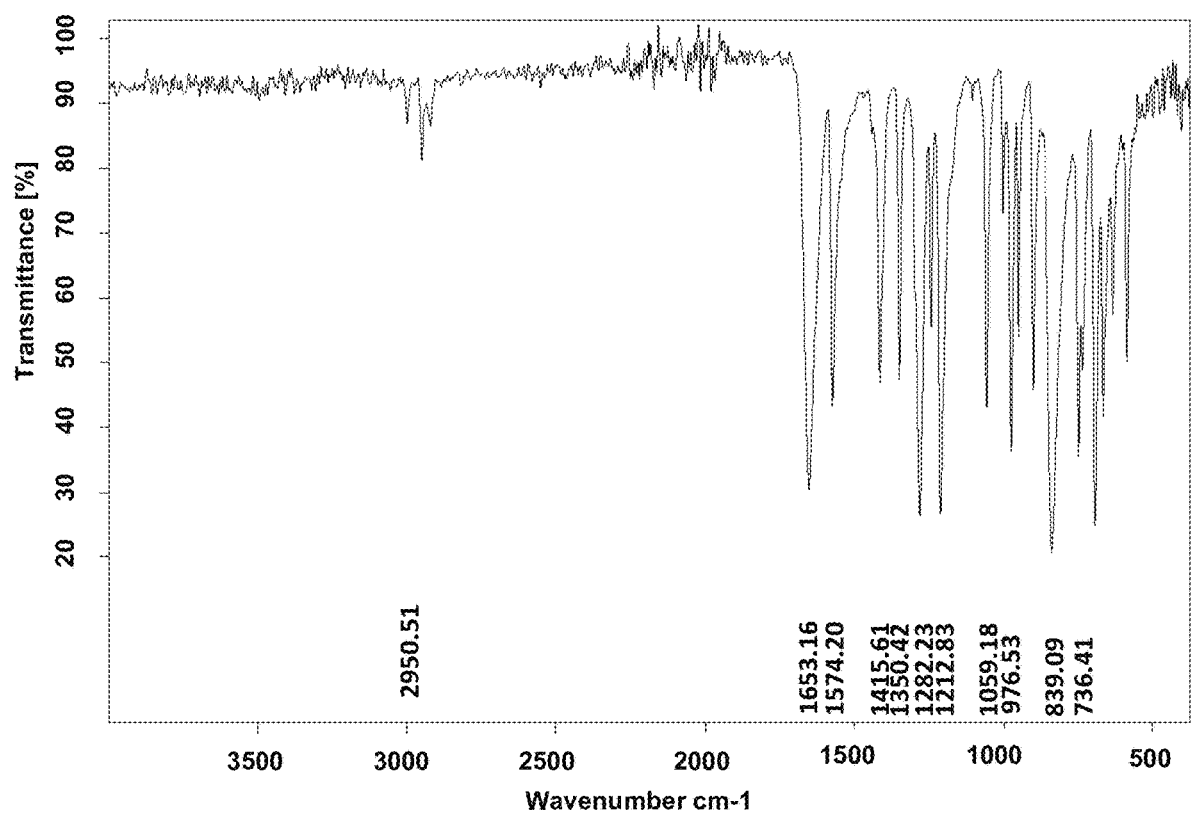
FIG. 11 is an infrared (IR) spectrum for [3,3'-bis(1,2,4-oxadiazole)]-5,5'-diylbis(methylene) dinitrate.
Figure 12:
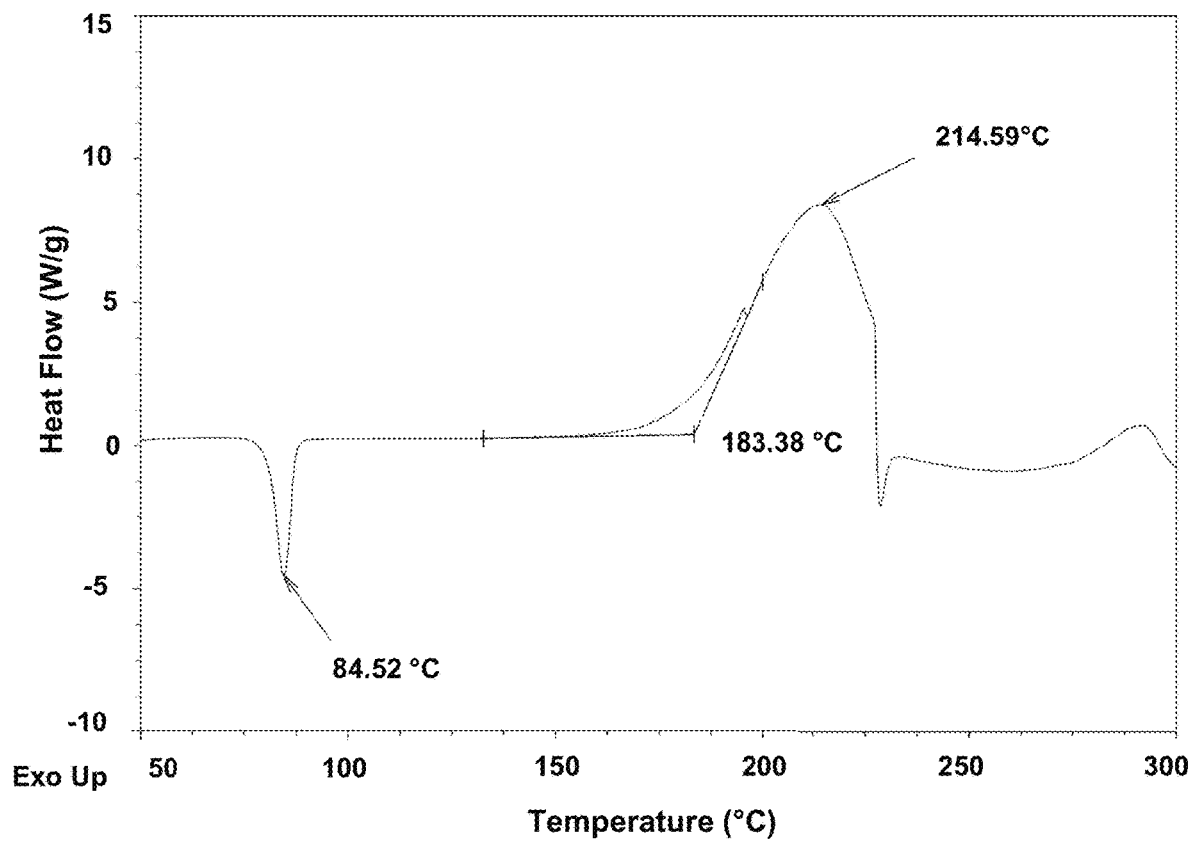
FIG. 12 is a differential scanning calorimetry (DSC) spectrum for [3,3'-bis(1,2,4-oxadiazole)]-5,5'-diylbis(methylene) dinitrate.

The following explanations of terms are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting, unless otherwise indicated. Other features of the disclosure are apparent from the following detailed description and the claims.

Although the operations of exemplary embodiments of the disclosed method may be described in a particular, sequential order for convenient presentation, it should be understood that disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under standard test conditions/methods. When directly and explicitly distinguishing embodiments from discussed prior art, the embodiment numbers are not approximates unless the word "about" is recited. Furthermore, not all alternatives recited herein are equivalents.

To facilitate review of the various embodiments of the disclosure, the following explanations of specific terms are provided. Certain functional group terms include a symbol "-" which is used to show how the defined functional group attaches to, or within, the compound to which it is bound. A person of ordinary skill in the art would recognize that the definitions provided below and the compounds and formulas included herein are not intended to include impermissible substitution patterns (e.g., methyl substituted with 5 different groups, and the like). Such impermissible substitution patterns are easily recognized by a person of ordinary skill in the art. In formulas and compounds disclosed herein, a hydrogen atom is present and completes any formal valency requirements (but may not necessarily be illustrated) wherever a functional group or other atom is not illustrated. For example, a phenyl ring that is drawn as

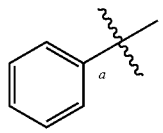

comprises a hydrogen atom attached to each carbon atom of the phenyl ring other than the "a" carbon, even though such hydrogen atoms are not illustrated. Any functional group disclosed herein and/or defined above can be substituted or unsubstituted, unless otherwise indicated herein.

Aldehyde: —C(O)H.

Aliphatic: A hydrocarbon group having at least one carbon atom to 50 carbon atoms ($C_{1-50}$), such as one to 25 carbon atoms ($C_{1-25}$), or one to ten carbon atoms ($C_{1-10}$), and which includes alkanes (or alkyl), alkenes (or alkenyl), alkynes (or alkynyl), including cyclic versions thereof, and further including straight- and branched-chain arrangements, and all stereo and position isomers as well. Aliphatic groups are distinct from aromatic groups.

Alkenyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon double bond, wherein the unsaturated monovalent hydrocarbon can be derived from removing one hydrogen atom from one carbon atom of a parent alkene. An alkenyl group can be branched, straight-chain, cyclic (e.g., cycloalkenyl), cis, or trans (e.g., E or Z).

Alkyl: A saturated monovalent hydrocarbon having at least one carbon atom to 50 carbon atoms ($C_{1-50}$), such as one to 25 carbon atoms ($C_{1-25}$), or one to ten carbon atoms ($C_{1-10}$), wherein the saturated monovalent hydrocarbon can be derived from removing one hydrogen atom from one carbon atom of a parent compound (e.g., alkane). An alkyl group can be branched, straight-chain, or cyclic (e.g., cycloalkyl).

Alkynyl: An unsaturated monovalent hydrocarbon having at least two carbon atom to 50 carbon atoms ($C_{2-50}$), such as two to 25 carbon atoms ($C_{2-25}$), or two to ten carbon atoms ($C_{2-10}$), and at least one carbon-carbon triple bond, wherein the unsaturated monovalent hydrocarbon can be derived from removing one hydrogen atom from one carbon atom of a parent alkyne. An alkynyl group can be branched, straight-chain, or cyclic (e.g., cycloalkynyl).

Amino: —$NR^aR^b$, wherein each of $R^a$ and $R^b$ independently is selected from hydrogen, aliphatic, heteroaliphatic, or aromatic.

Aromatic: A cyclic, conjugated group or moiety of, unless specified otherwise, from 5 to 15 ring atoms having a single ring (e.g., phenyl) or multiple condensed rings in which at least one ring is aromatic (e.g., naphthyl, indolyl, or pyrazolopyridinyl); that is, at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

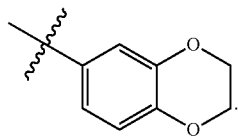 [SMILES: *c1ccc2c(c1)OCCO2]

However, in certain examples, context or express disclosure may indicate that the point of attachment is through a non-aromatic portion of the condensed ring system. For example,

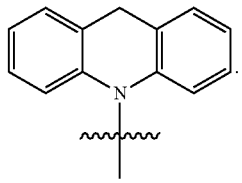 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Aromatic groups may be substituted with one or more groups other than hydrogen.

Aryl: An aromatic carbocyclic group comprising at least five carbon atoms to 15 carbon atoms ($C_5$-$C_{15}$), such as five to ten carbon atoms ($C_5$-$C_{10}$), having a single ring or multiple condensed rings, which condensed rings can or may not be aromatic provided that the point of attachment to a remaining position of the compounds disclosed herein is through an atom of the aromatic carbocyclic group. Aryl groups may be substituted with one or more groups other than hydrogen.

Carbonyl-Containing Compound: A compound used as a reagent in making an energetic compound embodiment, wherein the carbonyl-containing compound comprises at least one carbonyl group. In some embodiments, the carbonyl-containing compound has a structure of Formula VI as described herein.

Carboxyl: —C(O)OH.

Decomposition Temperature: The temperature at which a substance chemically decomposes and/or at least begins to decompose.

Detonation Velocity: The velocity at which a shock wave front travels through a detonated explosive.

Ester: —C(O)OR$^a$ or —OC(O)R$^a$, wherein R$^a$ is selected from aliphatic, heteroaliphatic, or aromatic.

Heteroaliphatic: An aliphatic group comprising at least one heteroatom to 20 heteroatoms, such as one to 15 heteroatoms, or one to 5 heteroatoms, which can be selected from, but not limited to oxygen, nitrogen, sulfur, silicon, boron, selenium, phosphorous, and oxidized forms thereof within the group. Alkoxy, ether, amino, disulfide, peroxy, and thioether groups are exemplary (but non-limiting) examples of heteroaliphatic. Heteroaliphatic groups are distinct from heteroaryl groups.

Heteroaryl: An aryl group comprising at least one heteroatom to six heteroatoms, such as one to four heteroatoms, which can be selected from, but not limited to oxygen, nitrogen, sulfur, silicon, boron, selenium, phosphorous, and oxidized forms thereof within the ring. Such heteroaryl groups can have a single ring or multiple condensed rings, wherein the condensed rings may or may not be aromatic and/or contain a heteroatom, provided that the point of attachment is through an atom of the aromatic heteroaryl group. Heteroaryl groups may be substituted with one or more groups other than hydrogen.

Hydroxyl Protecting Group: A functional group that can be used to replace a hydroxyl group (or at least replace the hydrogen atom thereof) during a synthetic method to prevent decomposition of and/or undesirable reactions with the hydroxyl group. Exemplary hydroxyl protecting groups can include silyl groups, ether groups, benzyl groups, acyl groups, benzoyl groups, and the like. Additional hydroxyl protecting groups are recognized by those of ordinary skill in the art with the benefit of the present disclosure, with several being disclosed in *Greene's Protective Groups in Organic Synthesis*, by Peter G. M. Wuts and Theodora W. Greene (Oct. 30, 2006), which is incorporated herein by reference.

Onset Temperature of Melting: The temperature at which a compound begins to melt.

Oxadiazole: An aromatic five-membered ring system comprising at least one oxygen atom and two nitrogen atoms. In some embodiments, the oxadiazole can be a 1,2,3-oxadiazole, a 1,2,4-oxadiazole, a 1,2,5-oxadiazole, or a 1,3,4-oxadiazole.

Oxazole: An aromatic five-membered ring system comprising at least one oxygen atom and one nitrogen atom. In some embodiments, an oxazole comprises at least one carbon atom between the oxygen and the nitrogen atom; however, some oxazole embodiments are isomers wherein the oxygen and the nitrogen atom are adjacent to one another.

Oxatriazole: An aromatic five-membered ring system comprising at least one oxygen atom and three nitrogen atoms.

Oxime: —CR$^a$=NOH, wherein R$^a$ is hydrogen, aliphatic, heteroaliphatic, or aromatic.

Plasticizer: A plasticizer enhances fluidity or plasticity when added to a formulation. Energetic plasticizers are used to improve physical properties, to act as a fuel, and to improve the overall energy yield of a formulation. In some embodiments, the energetic compound embodiments can serve as energetic plasticizers given their good density, reasonable sensitivity, low chemical reactivity, and high thermal stability, properties which are described in detail herein.

II. Introduction

Developing HEDMs with excellent performance and reasonable sensitivity is an overarching goal in the field of energetic materials, with high-energy-density melt-castable explosives being a particularly challenging area. Although a melt-cast material can have a melting point between 70 and 120° C., melting points below 100° C. can be beneficial. For example, this can allow for steam heating to be used at ambient pressure in casting operations, which can dramatically reduce costs in manufacturing. Other meaningful properties of a melt-castable explosive include low vapor pressure, a significant difference between the melting temperature and the decomposition temperature, high density, low sensitivity, and "green" and affordable synthesis. Traditional state-of-the-art melt-castable explosives have been TNT-based; however, TNT has fallen out of favor in the energetics community because of toxicity and environmental concerns. TNT is listed as a possible human carcinogen, and prolonged exposure to TNT may result in anemia and abnormal liver function.

As a stand-alone ingredient, TNT suffers from a relatively high vapor pressure, is susceptible to photolytic degradation, and is sensitive to reactions in an alkaline environment. Also concerning is the generation of red water and pink water, two types of wastewater that are generated from the TNT manufacturing process, which find their ways into the waste stream. Red water is waste generated during the TNT purification process (sulfitation). It is characterized by its alkaline pH of 8 and consists of a complex mixture of nitroaromatics and inorganic salts. Pink water is wash water from the TNT finishing process following sulfitation, in which the TNT is dried, flaked, and packaged. Pink water, which is acidic (pH ~3) is typically saturated with the amount of TNT that will dissolve in water and is produced as a result of equipment washing processes following demilitarization or munitions filling operations. The U.S. Environmental Protection Agency has declared TNT a pollutant and has pushed for its removal from military munitions.

The removal of TNT as an explosive ingredient has garnered some success militarily, as it has been replaced with melt-castable eutectic formulations based on dinitroanisole (DNAN). Unfortunately, DNAN has a low density of 1.52 gcm$^{-3}$ and a detonation velocity of only 5670 m s$^{-1}$, making it a significantly less powerful explosive than TNT (density of 1.65 g cm$^{-3}$ and a detonation velocity of 6900 m s$^{-1}$). Thus, there is an interest in developing higher-performing melt-castable ingredients that are not only more powerful than DNAN but also more powerful than TNT and less environmentally problematic and less toxic to human health. Also, previously investigated materials based on N-nitroxyalkyl- and N-azidoalkyl-substituted nitro-based heterocycles have been found to suffer from stability issues due to the inherent reactivity of the electrophilic ring.

Disclosed herein are embodiments of a new energetic compound that can be used for HEDMs as a high-energy melt-castable explosive and an energetic propellant plasticizing ingredient. The disclosed compound embodiments exhibit unique and desirable energetic properties, high decomposition temperatures, and/or impact/friction/electrostatic discharge (or ESD) sensitivities.

III. Energetic Compound Embodiments

Disclosed herein are energetic compound embodiments. In some embodiments, the energetic compound embodiments can be used as high-energy melt-castable explosives and/or as energetic propellant plasticizing ingredients. The energetic compound embodiments can have structures of Formula I below.

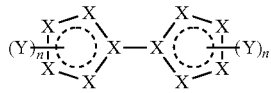

Formula I

With reference to Formula I, each X independently can be carbon, CH, nitrogen, NH, or oxygen; each Y independently can be -aliphatic-$ONO_2$, -aliphatic-OH, or -aliphatic-OPG, wherein the PG group is a hydroxyl protecting group; and each n independently can be an integer ranging from 0 to 4, such as 0, 1, 2, 3, or 4. The aliphatic portion of -aliphatic-$ONO_2$, -aliphatic-OH, or -aliphatic-OPG can be alkyl comprising 1 to 10 carbon atoms, such as 1 to 5 carbon atoms, or 1 to 4 carbon atoms, or 1 to 3 carbon atoms. In particular embodiments, each ring system illustrated in Formula I can be an aromatic ring system, such as a five-membered heteroaryl group. Variables in one five-membered ring of Formula I can be the same or different from the other five-membered ring of Formula I. In particular embodiments, the five-membered rings are identical to one another. In particular embodiments, at least one Y is -aliphatic-$ONO_2$ and at least one n is 1 to 4, such as 1. In some particular embodiments, each Y is —$CH_2ONO_2$. In some embodiments, and with respect to each five-membered ring, at least one X is oxygen and at least two X groups are nitrogen and/or NH. In particular disclosed embodiments, one of the five-membered rings can be an oxazole, an oxadiazole, or an oxatriazole (including any isomers thereof, such as an isoxazole, which is an oxazole isomer). In embodiments where one of the five-membered ring is an isoxazole, the other five-membered ring is not or is other than an isoxazole. In an independent embodiment, the compound is not 3,3'-bis-isoxazole-5,5'bis-methylene dinitrate, which has the structure illustrated below.

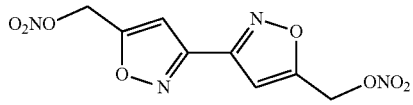

In particular disclosed embodiments, both five-membered rings are oxadiazoles. In yet additional embodiments, the energetic compound is symmetric. Exemplary oxazoles (including isoxazoles), oxadiazoles, and oxatriazoles are illustrated below. With respect to these structures, a person of ordinary skill in the art, with the benefit of the present disclosure, will recognize the positions on these structures that are capable of being bound to a Y group and/or another oxazole, oxadiazole, or oxatriazole as described for Formula I.

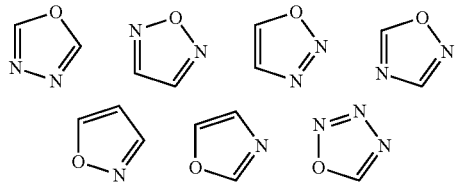

In particular disclosed embodiments, the energetic compound can have a structure of any one of Formulas II-V below.

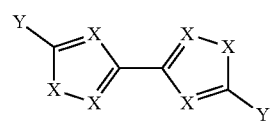

Formula II

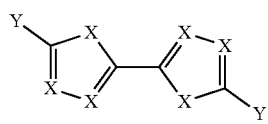

Formula III

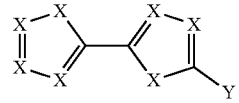

Formula IV

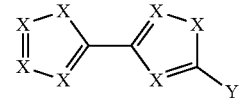

Formula V

With reference to Formulas II-IV, each X independently can be oxygen or nitrogen, accounting for proper valencies and each Y independently can be —$CH_2ONO_2$.

Representative energetic compound embodiments are illustrated below:

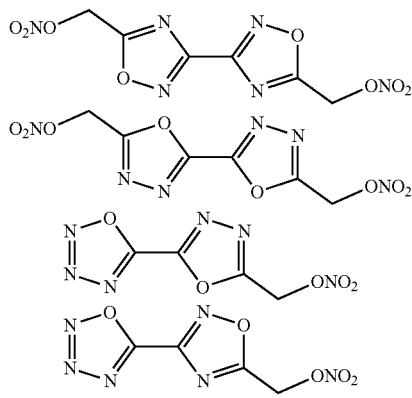

-continued

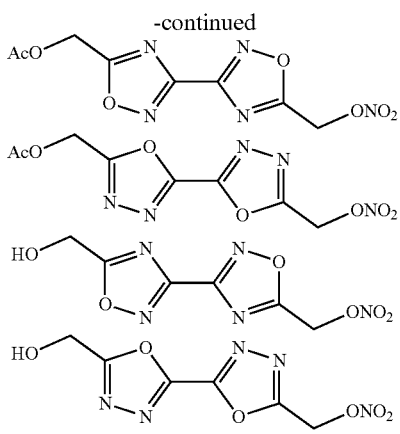

Also disclosed herein are intermediate compounds that can be prepared in methods used to make the energetic compound embodiments. These compounds are described in the Formulas above and exemplary embodiments of such compounds are provided below.

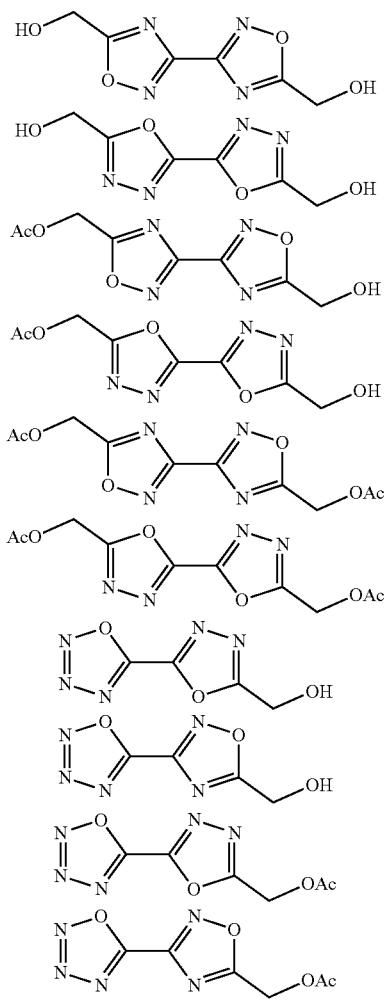

Compound embodiments disclosed herein can have properties that facilitate their use as energetic compounds. In some embodiments, energetic compound embodiments have decomposition temperatures ranging from 120° C. to 200° C., such as 130° C. to 195° C., or 140° C. to 195° C. In some embodiments, the energetic compound is a bis-oxadiazole dinitrate that has a decomposition temperature of 189° C. and/or a thermal onset of decomposition temperature of 183° C. (or 183.4° C.). In some embodiments, the energetic compound has an onset temperature of melting that ranges from greater than 80° C. to 85° C., such as greater than 81° C. to 84° C., or 82° C. to 83° C. In some embodiments, the onset temperature of melting is 82° C. In view of these melting point and decomposition temperature ranges, the energetic compound embodiments of the present disclosure are suitable for use as a melt-castable explosive material in some embodiments.

Compound embodiments disclosed herein can also have explosive properties that facilitate their use as energetic compounds. In some embodiments, the energetic compound has an explosive density ranging from greater than 1.75 g/cm³ to 2 g/cm³, such as 1.78 g/cm³ to 1.90 g/cm³, or 1.80 g/cm³ to 1.85 g/cm³. In some embodiments, the energetic compound exhibits a detonation velocity greater than 8000 m/s to 8200 m/s, such as 8050 m/s to 8150 m/s, or 8100 m/s to 8125 m/s. In yet additional embodiments, the energetic compound can exhibit detonation pressures ranging from greater than 27.0 GPa to 30.0 GPa, such as greater than 28.0 GPa to 29.0 GPa, or 28.1 GPa to 29, GPa, or 28.2 GPa to 28.9 GPa.

In yet additional embodiments, compound embodiments disclosed herein exhibit lower sensitivities to impact, friction, and/or ESD sensitivity (or combinations thereof) as compared to conventional explosive materials (e.g., RDX).

IV. Methods of Making Energetic Compound Embodiments

Disclosed herein are embodiments of a method for making the energetic compound embodiments of the present disclosure. In some embodiments, the method comprises exposing a bis-oxadiazole product to a nitrating agent to provide a bis-oxadiazole dinitrate. In such embodiments, the bis-oxadiazole product can have a structure represented by the formula illustrated below:

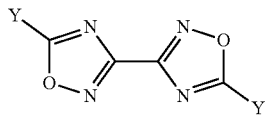

wherein each Y independently is aliphatic-OH or aliphatic-OPG, wherein PG is a hydroxyl protecting group. In some such method embodiments, the nitrating agent is HNO₃. In additional embodiments, the method can further comprise making the bis-oxadiazole product by combining a diaminoglyoxime product with a carbonyl-containing reagent to form a reaction mixture and heating the reaction mixture at a temperature above room temperature. The diaminoglyoxime product can have a structure

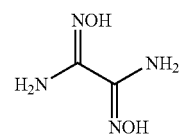

and the carbonyl-containing reagent has a structure of Formula VI as described below. In yet additional embodiments, the method can further comprise making the diaminoglyoxime product by combining a di-aldehyde precursor compound with a hydroxylamine. In some such embodiments, the di-aldehyde precursor compound is oxalaldehyde and the hydroxylamine is $NH_2OH$, or an aqueous composition thereof.

In some embodiments, the method described in Scheme 1, below, can be used to make the energetic compound. In such embodiments, the method can comprise combining a di-aldehyde precursor compound with a hydroxylamine, typically provided as an aqueous solution, to provide a diaminoglyoxime (DAG) product. In some embodiments, the method comprises combining a DAG product with a carbonyl-containing reagent and a base to provide reaction mixture that produces a bis-oxadiazole product. In some embodiments, the method can further comprise heating the reaction mixture to provide the bis-oxadiazole product. In some embodiments, the bis-oxadiazole product is then nitrated using a suitable nitrating agent to provide a bis-oxadiazole dinitrate. With reference to Scheme 1, each Y' indicates that the Y group of the precursor formula has been functionalized to provide a nitrate ester moiety. In some embodiments, if the ester group comprises a protected OH group, then the method can further comprise a deprotection step to remove the protecting group that protects the OH group. In some embodiments, any such deprotection step can be added as an additional step or can be combined with a step of the method illustrated below in Scheme 1.

Representative carbonyl-containing reagents can comprise a backbone comprise an ester functional group or an acyl halide group (halogen-C(O)—), an aliphatic functional group, and an OH functional group, or a protected version thereof. In particular disclosed embodiments, the carbonyl-containing reagent can have a structure of Formula VI below.

Formula VI

With reference to Formula VI, Z is alkoxy or halogen (e.g., Cl, F, I, or Br), and Y can be as described above for any one or more of Formulas I-V. In particular disclosed embodiments where Z is alkoxy, the alkoxy group can be lower alkoxy, such as methoxy, ethoxy, propoxy, butoxy, pentoxy, or hexyloxy; and Y is -aliphatic-OH, such as —$CH_2OH$ or a protected version thereof (such as —$CH_2OAc$ or the like). In exemplary embodiments, the carbonyl-containing reagent is selected from methyl 2-hydroxyacetate or methyl 2-acetoxyacetate.

Representative bases that can be used in some method embodiments include, but are not limited to, metal carbonate bases, such as potassium carbonate, sodium carbonate, cesium carbonate, or combinations thereof; metal bicarbonates, such as sodium bicarbonate, potassium bicarbonate, cesium bicarbonate, or combinations thereof; trialkyl amines, such as triethylamine or diisopropylethylamine or combinations thereof; or any combination of such bases. Representative nitrating agents can include, but are not limited to, concentrated and/or dilute forms of nitric acid. In some embodiments, the nitrating agent is nitric acid that is used neat or that has been diluted with water, such 50%-99% nitric acid, or 60% to 95% nitric acid, or 70% to 90% nitric acid. In some embodiments, the nitrating agent is 100% nitric acid or 90% nitric acid. In yet additional embodiments, the nitrating agent can be provided as a mixed acid system, such as a combination of nitric acid and another acid, such as sulfuric acid.

Representative method embodiments for making energetic compound embodiments of the present disclosure are illustrated in Schemes 2-5 below. Details regarding the reagents and reaction conditions used in these representative embodiments are described in the Examples section of the present disclosure.

Scheme 1

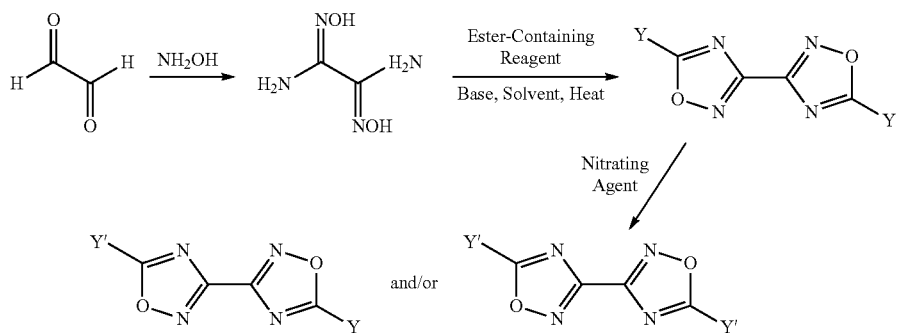

Scheme 2

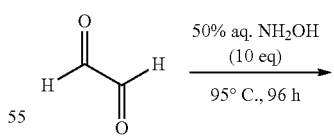

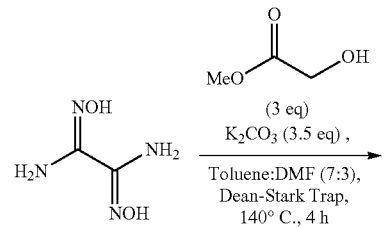

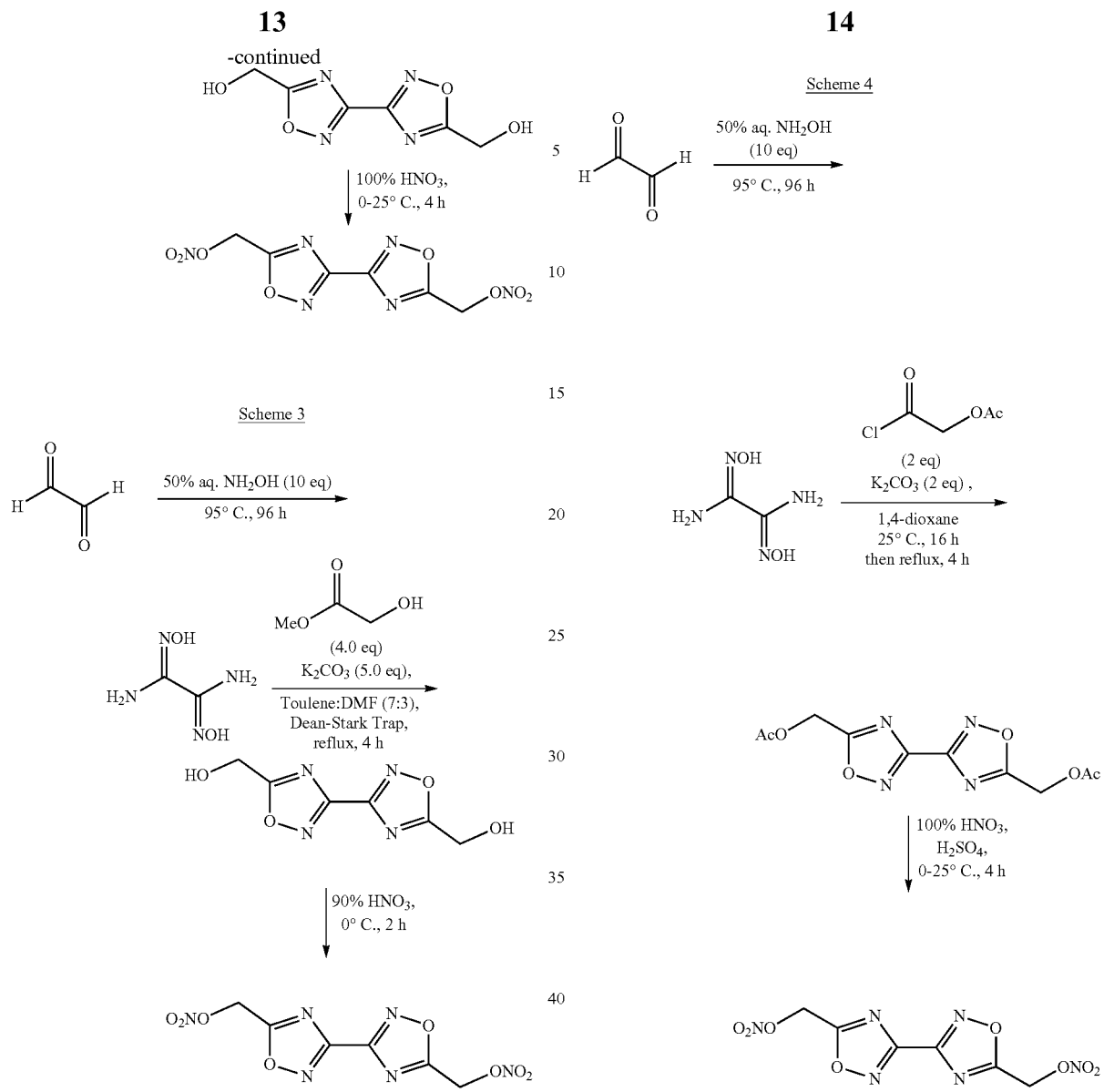
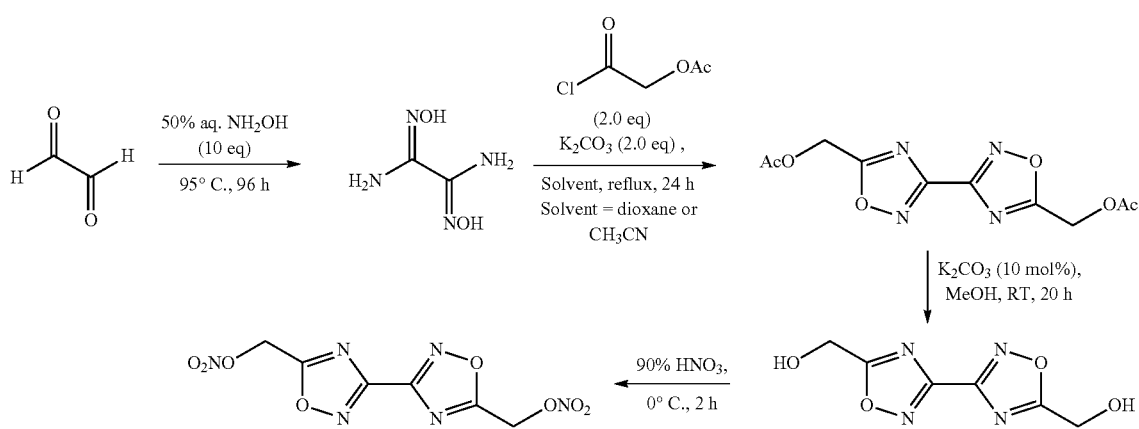

In some embodiments, the method can comprise steps suitable for making other oxadiazole rings, such as a bis-1,3,4-oxadiazole ring system, that can comprise (or that can be functionalized to comprise) one or more nitro groups and/or one or more nitrate ester groups. In some embodiments, the method can comprise combining a 1,3,4-oxadiazole-containing hydrazide compound with a carboxyl-containing compound under suitable conditions, thereby providing a bis-1,3,4-oxadiazole skeleton, which can be nitrated with nitric acid (or a mixed acid system) to provide one or more nitro groups and/or one or more nitrate ester groups.

V. Methods of Use

The compound embodiments disclosed herein can be used as energetic materials and/or as additives that are combined with one or more additional energetic compounds or compositions. In particular disclosed embodiments, the compound embodiments can be used as high-energy melt-castable explosives and in some embodiments can be replacements for TNT-based, RDX-based, furazan-based, furoxan-based, and DNAN-based melt-castable formulations. In additional embodiments, the disclosed energetic compound embodiments can be used as energetic plasticizers, such as energetic plasticizers to replace diethylene glycol dinitrate (DEGDN) and triethylene glycol dinitrate (TEGDN) in double-base propellant formulations and/or to replace non-energetic phthalate-based, adipate-based, and triacetin-based propellant plasticizer ingredients in rocket and gun propellant applications. The energetic compound embodiments disclosed herein also can be used as energetic ingredients that assist in making up the general formulation of double-based propellants. In additional embodiments, the energetic compound embodiments can be used as RDX replacements in propellant formulations to improve wetting and/or plasticization with nitrocellulose (or "NC"). The energetic compound embodiments disclosed herein can provide enhanced energy and processing safety/handling to such propellant compositions. Additionally, because the energetic compound embodiments are able to plasticize NC more effectively, higher nitrogen content NC can be used, thus improving resultant mechanical properties. In yet additional embodiments, the energetic compound embodiments can be used to improve ρ-specific impulse (or "ρ-$I_{sp}$"). In some embodiments, the energetic compound embodiments of the present disclosure can be mixed with other energetic materials, such as energetic materials currently used in the art, such as RDX, HMX, CL-20, and the like, to produce melt-castable explosive compositions.

In yet additional embodiments, the energetic compound embodiments of the present disclosure can be used in pressed and/or extruded dynamite formulations where heat of explosion is often controlled only by alteration of nitroglycerin content. The use of an insensitive, yet energetic plasticizer with reduced volatility, such as an embodiment of the energetic compound disclosed herein, can enhance the manufacture, transportation, and storage of dynamites containing such an energetic compound embodiment. In yet additional embodiments, energetic compound embodiments of the present disclosure can be used for underground mining and deep petroleum fracking, particular in view of their thermal stability, lower vapor pressure, and/or slow aging. Such embodiments therefore can be useful in tactical platforms that are exposed to large thermal extremes or extended periods of thermal stress and can exhibit lower migration rates of the propellant within a liner and/or into the external environment.

Energetic compound embodiments of the present disclosure typically are less volatile and more thermally robust than other energetic compounds, such as diethyleneglycol dinitrate (or "DEGDN"). Without being limited to a particular theory, it currently is believed that the Lewis basic nature of some energetic compound embodiments may promote their ability to serve as better wetting ingredients, which may plasticize other energetic materials (e.g., NC) more effectively. For example, the lower vapor pressure and potential favorable interactions of certain energetic compound embodiments with an extensive amount of NC may improve slow cook-off and bullet/fragment impact, both of which are driven by gas phase reactions. Additionally, compound embodiments of the present disclosure can exhibit molecular interactions with a plasticizer matrix, which can promote homogenous interactions and thereby decrease sensitivity of a propellant comprising an energetic compound embodiment.

In certain embodiments, the energetic compound has a zero oxygen balance with respect to carbon monoxide (CO), high density, and possesses properties that facilitates its use as energetic plasticizer and wetting agent/energetic surfactant. Certain compound embodiments are soluble in organic solvents (e.g., acetone), but are insoluble in water and certain compound embodiments possess at least some Lewis base activity (e.g., N—O oxadiazole linkages) to interact with electrophilic binders and solid fillers. Certain compound embodiments also exhibit energetic, electrophilic properties that facilitate solubility in the lacquer in double-base lacquers and/or nitrate ester-based lacquers.

VI. Overview of Several Embodiments

Disclosed herein are embodiments of a compound having a structure of Formula I,

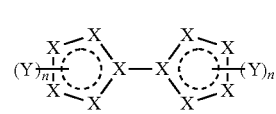

Formula I wherein each X independently is selected from carbon, CH, nitrogen, NH, or oxygen; each Y independently is selected from aliphatic-ONO$_2$, aliphatic-OH, or aliphatic-OPG, wherein PG is a hydroxyl protecting group; and each n independently is an integer ranging from 0 to 4; provided that (i) at least one n is an integer ranging from 1 to 4; and (ii) the compound is not

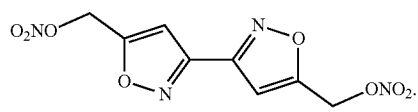

In some embodiments, each five-membered ring of Formula I independently is aromatic.

In any or all of the above embodiments, each five-membered ring of Formula I independently is heteroaryl and is an oxadiazole, an oxazole, an oxatriazole, or an isomer thereof.

In any or all of the above embodiments, each five-membered ring of Formula I is an oxadiazole.

In any or all of the above embodiments, each Y independently is aliphatic-ONO$_2$, wherein aliphatic is an alkyl group comprising 1 to 5 carbon atoms. In some embodiments, the alkyl group is a methylene group.

In any or all of the above embodiments, each Y is —CH$_2$ONO$_2$ and each n is 1.

In any or all of the above embodiments, the compound can have a structure of any one or more of Formulas II-V

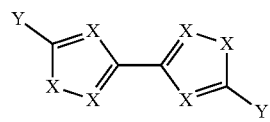

Formula II

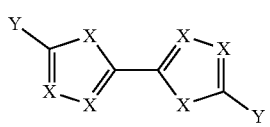

Formula III

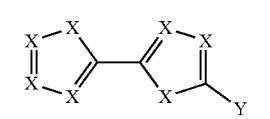

Formula IV

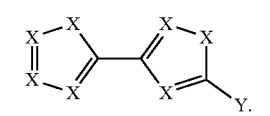

Formula V

In any or all of the above embodiments, each Y independently is —CH$_2$ONO$_2$.

In any or all of the above embodiments, the compound is selected from

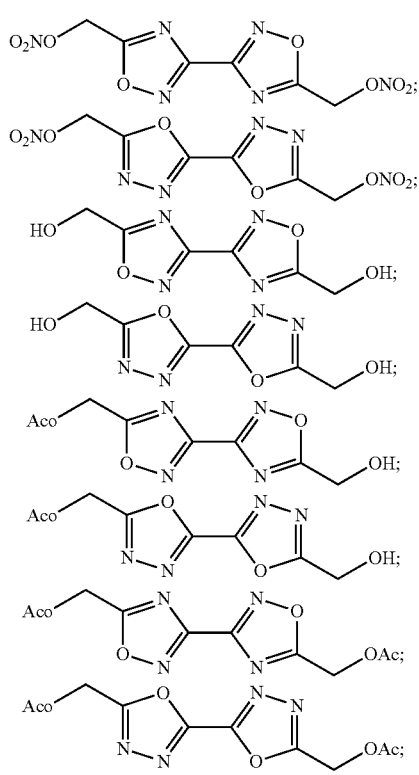

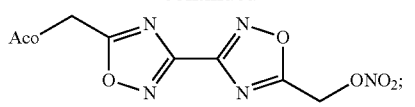

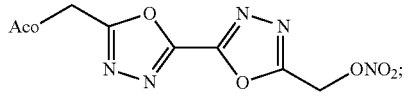

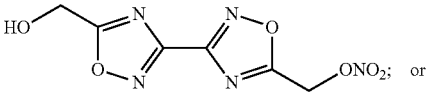

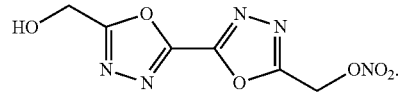

In any or all of the above embodiments, the compound is

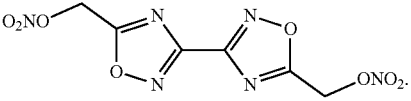

In any or all of the above embodiments, the compound has a decomposition temperature ranging from 140° C. to 195° C.

In any or all of the above embodiments, the compound has an onset temperature of melting that ranges from greater than 80° C. to 85° C.

In any or all of the above embodiments, the compound has an explosive density ranging from greater than 1.75 g/cm$^3$ to 2 g/cm$^3$.

In any or all of the above embodiments, the compound has a detonation velocity greater than 8000 m/s to 8200 m/s.

Also disclosed herein are embodiments of a method, comprising exposing a bis-oxadiazole product to a nitrating agent to provide a bis-oxadiazole dinitrate.

In any or all of the above embodiments, the bis-oxadiazole product has a structure of a formula

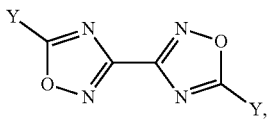

wherein each Y independently is aliphatic-OH or aliphatic-OPG, wherein PG is a hydroxyl protecting group.

In any or all of the above embodiments, the nitrating agent is HNO$_3$.

In any or all of the above embodiments, the method further comprises making the bis-oxadiazole product by combining a diaminoglyoxime product with a carbonyl-containing reagent to form a reaction mixture and heating the reaction mixture at a temperature above room temperature.

In any or all of the above embodiments, the diaminoglyoxime product has a structure

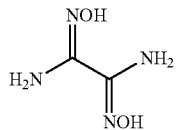

and the carbonyl-containing reagent has a structure of a formula

wherein Z is alkoxy or halogen and Y is aliphatic-OH or aliphatic-OPG, wherein PG is a hydroxyl protecting group.

In any or all of the above embodiments, the solvent is a mixture of DMF and toluene, or a dioxane solvent, or acetonitrile.

In any or all of the above embodiments, the method further comprises making the diaminoglyoxime product by combining a di-aldehyde precursor compound with a hydroxylamine.

In any or all of the above embodiments, the di-aldehyde precursor compound is oxalaldehyde and the hydroxylamine is $NH_2OH$, or an aqueous composition thereof.

Also disclosed herein are embodiments of a method of using the compound of any one or all of the above compound embodiments, comprising making a melt-castable explosive composition and/or a propellant plasticizer composition with the compound.

VII. Examples

General Methods: Chemicals and solvents were used as received from Sigma-Aldrich. Diaminoglyoxime was synthesized as described herein. $^1H$ and $^{13}C$ NMR spectra were recorded using an Anasazi 90 MHz instrument. The chemical shifts quoted in parts per million in the text refer to typical standard tetramethylsilane in $CDCl_3$ as the solvent. Infrared spectra were measured with a Bruker Alpha-P FTIR instrument. Melting and decomposition temperatures were measured at a heating rate of 5° C./minute using a TA Instruments Q10 DSC instrument. Single-crystal X-ray diffraction studies were performed with a SuperNova Dualflex diffractometer containing an EosS2 charge-coupled device detector and a Mo Kα radiation source (λ=0.71073 Å).

Example 1

In this example, an energetic compound embodiment was made using the method described below.

Scheme 6

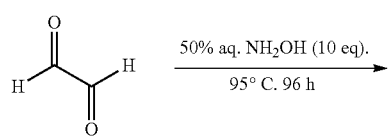

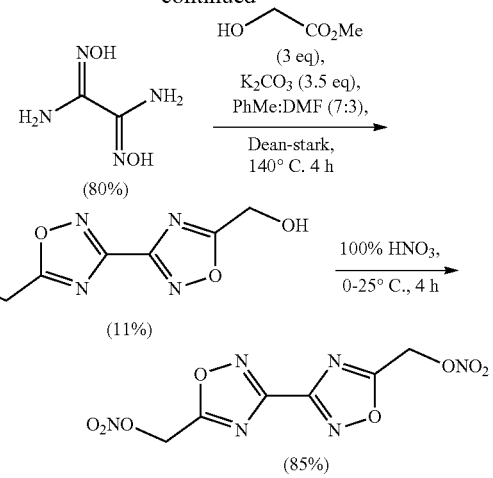

As summarized in Scheme 6, the synthesis of energetic compound initially commenced with condensation of glyoxal with 50% aqueous hydroxylamine to afford diaminoglyoxime. Use of an all-aqueous system when preparing DAG as opposed to the use of a hydroxyammonium chloride/NaOH system was found to dramatically reduce the exothermic nature of the reaction profile. Treatment of DAG with methyl glycolate in the presence of base at high temperature, afforded bis(1,2,4-oxadiazole). In some embodiments, it was found that the yield could be improved to 11% if a solution of DAG in DMF/toluene was added over the course of 4 hours. In yet additional examples, the DMF/toluene solvent system can be replaced with acetonitrile. Nitration of bis(1,2,4-oxadiazole) with 100% $HNO_3$ yielded the energetic bisoxadiazole compound in 85% yield.

Example 2

In this example, an energetic compound embodiment was made using the method described below.

Scheme 7

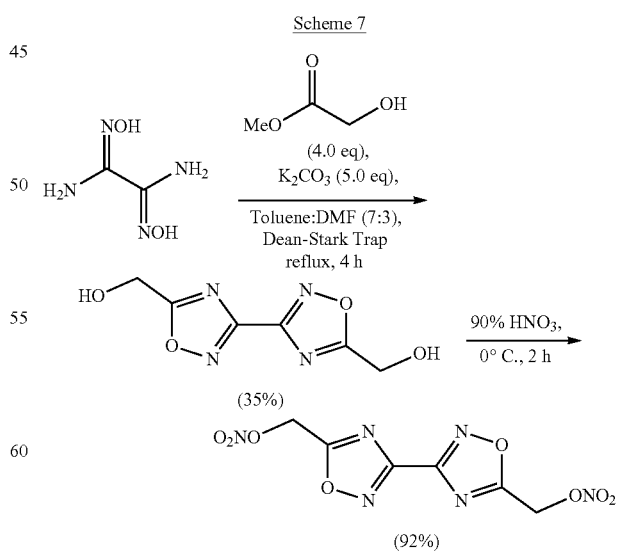

Similar conditions to those described in Example 1 were used in this embodiment, except that the bis(1,2,4-oxadiazole) intermediate was nitrated in 90% HNO$_3$ to afford the energetic bisoxadiazole compound in 92% yield. Interestingly, 90% HNO$_3$ provided the energetic bisoxadiazole compound in the needle-like morphology. Recrystallization of the energetic bisoxadiazole compound from acetone/H$_2$O via a solvent/anti-solvent method can provide the energetic bisoxadiazole compound in a cubic/platelet morphology.

Example 3

In this example, an additional method embodiment is described for making an energetic bisoxadiazole compound.

Scheme 8

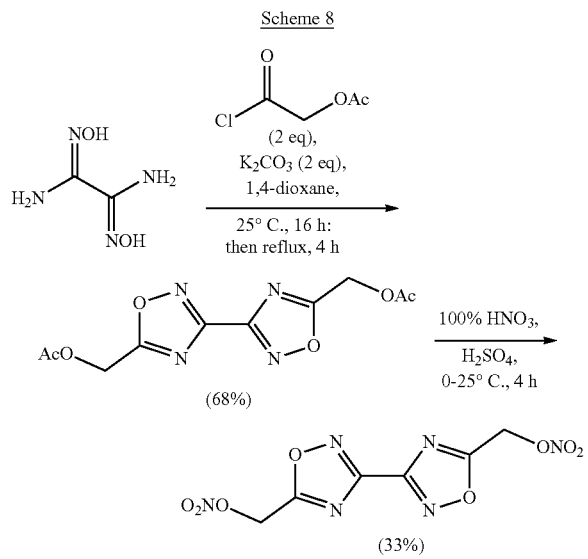

In this example, the DAG product was made using a method similar to that described above for Example 1. After obtaining the DAG compound, acetoxyacetyl chloride was added dropwise to a suspension of the DAG compound and K$_2$CO$_3$ in 1,4-dioxane at room temperature followed by stirring overnight afforded a bis(O-acyl) intermediate, which underwent double cyclization at the refluxing temperature to provide an acylated version of the energetic bis(1,2,4-oxadiazole) compound. The acylated compound was reacted under mixed acid conditions to promote nitrolysis and afford the bis-oxadiazole compound. In yet additional examples, the dioxane solvent can be replaced with acetonitrile.

Example 4

In this example, an additional method embodiment is described for making an energetic bisoxadiazole compound.

Scheme 9

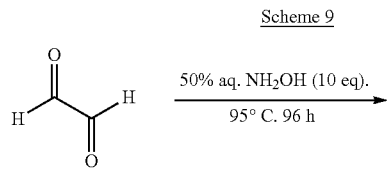

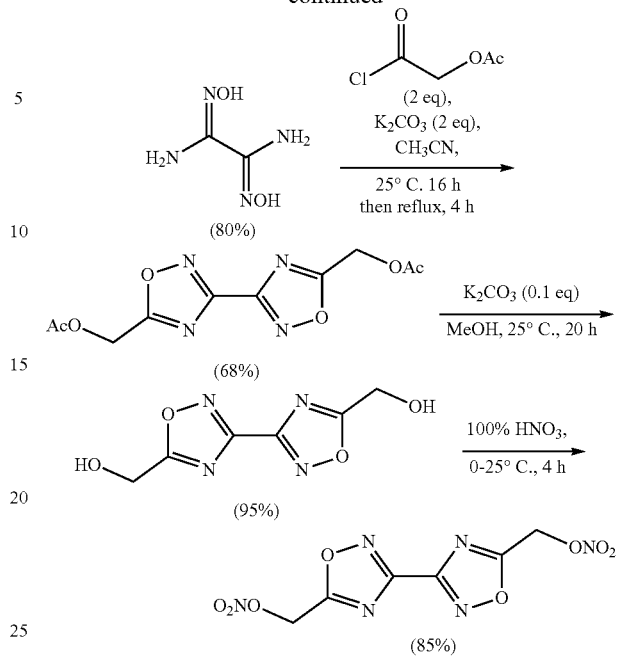

In this example, different conditions for converting the acylated version of the energetic bis(1,2,4-oxadiazole) compound to the energetic bis-oxadiazole compound were used. Rather than treating the acylated compound to mixed acid conditions, the acyl groups were removed using K$_2$CO$_3$ to provide the resulting bis-alcohol product, which was then treated with HNO$_3$ to provide the energetic bis(1,2,4-oxadiazole) compound in good yield. Additionally, the dioxane solvent used in Example 3 was replaced with acetonitrile, which can be more environmentally acceptable.

In particular, [3,3'-Bis(1,2,4-oxadiazole)]-5,5'-diylbis (methylene) was made according to the following procedure: To a 2 L round-bottom flask equipped with a stir bar were sequentially added 1 L of acetonitrile, the DAG (15.0 g, 0.127 mol, 1.00 equivalents), and K$_2$CO$_3$ (35.1 g, 0.254 mol, 2.00 equivalents). The flask was fitted with a pressure-equalizing liquid addition funnel, and a solution of acetoxyacetyl chloride (35.4 g, 27.9 mL, 0.254 mol, 2.00 equiv) in 200 mL of CH$_3$CN was added dropwise over 2 hours. The reaction mixture was stirred overnight at ambient temperature, and the flask was then fitted with a reflux condenser. The reaction mixture was heated to reflux, stirred for 4 hours, and then cooled to room temperature. The solid was collected by Büchner filtration and discarded. The mother liquor was transferred to a 2 L round-bottom flask and concentrated in vacuo to afford a crude solid. The crude solid was purified by trituration with 500 mL of H$_2$O. The solid was collected by Büchner filtration and oven-dried at 60° C. overnight to afford 24.4 g of bis(1,2,4-oxadiazole) (68% yield) as a white powder. T$_{melt}$=107.5° C.; $^1$H NMR (90 MHz, DMSO-d$_6$) δ 5.53 (s, 4H), 2.18 (s, 6H); $^{13}$C NMR (90 MHz, DMSO-d$_6$) δ 176.91, 169.84, 159.37, 56.45, 20.09; IR (neat) cm-1 1745.23 (s), 1577.13 (m), 1208.08 (s). See FIGS. 1-4 for the $^1$H NMR spectrum, the $^{13}$C NMR spectrum, the IR spectrum, and the DSC trace, respectively, for [3,3'-Bis(1,2,4-oxadiazole)]-5,5'-diylbis(methylene).

[3,3'-Bis(1,2,4-oxadiazole)]-5,5'-diyldimethanol was made according to the following procedure: To a 250 mL round-bottom flask equipped with a stir bar were sequentially added 50 mL of MeOH, [3,3'-Bis(1,2,4-oxadiazole)]-5,5'-diylbis(methylene) (24.0 g, 85.1 mmol, 1.00 equiv), and $K_2CO_3$ (1.18 g, 8.51 mmol, 0.100 equivalents). The reaction mixture was stirred at ambient temperature for 48 hours and then concentrated in vacuo to give a crude solid, which was purified by trituration with 200 mL of $H_2O$. The solid was collected by Büchner filtration and oven-dried at 60° C. overnight to afford 16.0 g of the diol (95% yield) as a white powder. $T_{melt}$=197.8° C.; $T_{dec}$=231.5° C. (onset), 278.2° C. (peak); $^1H$ NMR (90 MHz, DMSO-$d_6$) δ 6.16 (s, 2H), 4.87 (s, 4H); $^{13}C$ NMR (90 MHz, DMSO-$d_6$) δ 178.50, 156.94, 52.74; IR (neat) cm$^{-1}$ 3339.57 (w), 1575.77 (m), 1431.04 (m), 1202.56 (m), 1081.27 (s). See FIGS. 5-8 for the $^1H$ NMR spectrum, the $^{13}C$ NMR spectrum, the IR spectrum, and the DSC trace, respectively, for [3,3'-Bis(1,2,4-oxadiazole)]-5,5'-diyldimethanol.

[3,3'-Bis(1,2,4-oxadiazole)]-5,5'-diylbis(methylene) dinitrate was made according to the following procedure: To a 250 mL round-bottom flask immersed in an ice bath was added 100 mL of 100% $HNO_3$. After the nitric acid was chilled to 0° C., the diol product described above (20.0 g, 101.0 mmol, 1.00 equivalent) was added in four equal portions over 1 hour. After the addition was complete, the reaction mixture was stirred for 4 hours, during which time the ice bath was allowed to melt, and the reaction mixture was allowed to warm to ambient temperature. The reaction mixture was poured onto crushed ice with stirring. After 1 hour, the solid was collected by Büchner filtration and air-dried in a well-ventilated fume hood to afford 24.7 g of the dinitrate product (85% yield) as a white powder. $T_{melt}$=84.5° C.; $T_{dec}$=183.4° C. (onset), 214.6° C. (peak); $^1H$ NMR (90 MHz, DMSO-$d_6$) δ 6.16 (s, 4H); $^{13}C$ NMR (90 MHz, DMSO-$d_6$) δ 175.48, 159.43, 64.26; IR (neat) cm$^{-1}$ 2950.51 (w), 1653.16 (s), 1574.20 (m), 1415.61 (m), 1350.42 (m), 1282.23 (s), 1212.83 (s), 1059.18 (m). See FIGS. 9-12 for the $^1H$ NMR spectrum, the $^{13}C$ NMR spectrum, the IR spectrum, and the DSC trace, respectively, for [3,3'-Bis(1,2,4-oxadiazole)]-5,5'-diylbis(methylene) dinitrate.

Example 5

Scheme 10

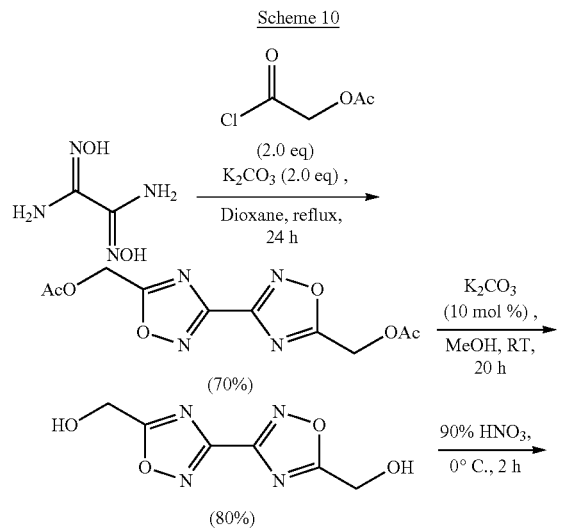

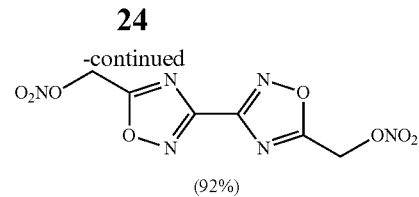

(92%)

In this example, an energetic compound embodiment was made using the method described in Example 3, except that 90% $HNO_3$ was used for the nitration step and removal of the acyl groups was conducted using conditions similar to those described in Example 4. Interestingly, 90% $HNO_3$ provided the energetic bisoxadiazole compound in the needle-like morphology. Recrystallization of the energetic bisoxadiazole compound from acetone/$H_2O$ via a solvent/anti-solvent method can provide the energetic bisoxadiazole compound in a cubic/platelet morphology.

Example 6

The physical properties and calculated explosive performance of [3,3'-Bis(1,2,4-oxadiazole)]-5,5'-diylbis(methylene) dinitrate are provided in Table 1. [3,3'-Bis(1,2,4-oxadiazole)]-5,5'-diylbis(methylene) dinitrate is CO oxygen-balanced and has a melting point of 84.5° C. and a thermal onset of decomposition at 183.4° C. Thus, it can be classified as a potential stand-alone melt-castable explosive material. [3,3'-Bis(1,2,4-oxadiazole)]-5,5'-diylbis(methylene) dinitrate out performs TNT in many categories by a wide margin, which is significant since the latter material is considered the benchmark for melt-castable explosives. The experimental density and theoretical detonation velocity of [3,3'-bis(1,2,4-oxadiazole)]-5,5'-diylbis(methylene) dinitrate are significantly higher than those of TNT, with a theoretical detonation pressure ca. 50% higher than that of TNT, even surpassing the performance of Composition B, a high-performance melt-castable formulation comprising RDX and TNT. The 1,2,4-oxadiazole moieties possess weak Lewis basic character as well as maximum pendant alkyl nitrate functionality. Hence, this material may also serve as an energetic plasticizer in nitrate-based formulations, potentially reducing volatility and migration during thermal and mechanical shock events.

TABLE 1

Physical properties and performance of 2 compared to TNT and Composition B.

| Data category | 2 | TNT | Composition B |
|---|---|---|---|
| $T_m$ [° C.][a] | 84.5 | 80.4 | 78.0-80.0 |
| $T_{dec}$ [° C.][b] | 183.4 | 295.0 | 200.0 |
| $\Omega_{CO2}$ [%][c] | −33.3 | −74.0 | — |
| $\Omega_{CO}$ [%][d] | 0 | −24.7 | — |
| ρ [gcm$^{-3}$][e] | 1.832 | 1.65 | 1.68-1.74 |
| $P_{cj}$ [GPa][f] | 29.4 | 20.5 | 26.0-28.0 |
| $V_{det}$ [ms$^{-1}$][g] | 8180 | 6950 | 7800-8000 |
| $I_{sp}$ [s][h] | 236.0 | — | — |
| $\Delta_f H°$ [kJ mol$^{-1}$][i] | −79.4 | −59.3 | — |

[a]$T_m$ = onset temperature of melting;
[b]$T_{dec}$ = onset temperature of melting;
[c]$\Omega_{CO2}$ = $CO_2$ oxygen balance;
[d]$\Omega_{CO}$ = CO oxygen balance;
[e]ρ = derived density from X-ray data;
[f]$P_{cj}$ = detonation pressure;
[g]$V_{det}$ = detonation velocity;
[h]$I_{sp}$ = specific impulse;
[i] $\Delta_f H°$ = molar enthalpy of formation.

The sensitivities of [3,3'-bis(1,2,4-oxadiazole)]-5,5'-diyl-bis(methylene) dinitrate toward impact, friction, and electrostatic discharge (ESD) were determined and compared with those of the commonly handled and processed explosive RDX (Table 2). [3,3'-Bis(1,2,4-oxadiazole)]-5,5'-diylbis(methylene) dinitrate was found to exhibit lower sensitivities to impact and friction and an identical ESD sensitivity compared to RDX and is therefore deemed to be a relatively safe material to handle. The relatively low sensitivities of [3,3'-bis(1,2,4-oxadiazole)]-5,5'-diylbis(methylene) dinitrate to impact and friction are noteworthy since there is a common belief among many in the energetic materials community that nitrate-based materials possess high sensitivities to impact and friction.

TABLE 2

Sensitivities of [3,3'-bis(1,2,4-oxadiazole)]-5,5'-diylbis(methylene) dinitrate as compared with RDX

| Compound | IS[a] | FS[b] | ESDS[c] |
|---|---|---|---|
| RDX | 6.2 | 156 | 0.125 |
| [3,3'-bis(1,2,4-oxadiazole)]-5,5'-diylbis(methylene) dinitrate | 8.7 | 282 | 0.125 |

[a]IS = impact sensitivity.
[b]FS = friction sensitivity.
[c]ESDS = electrostatic discharge sensitivity.

Figure 13:
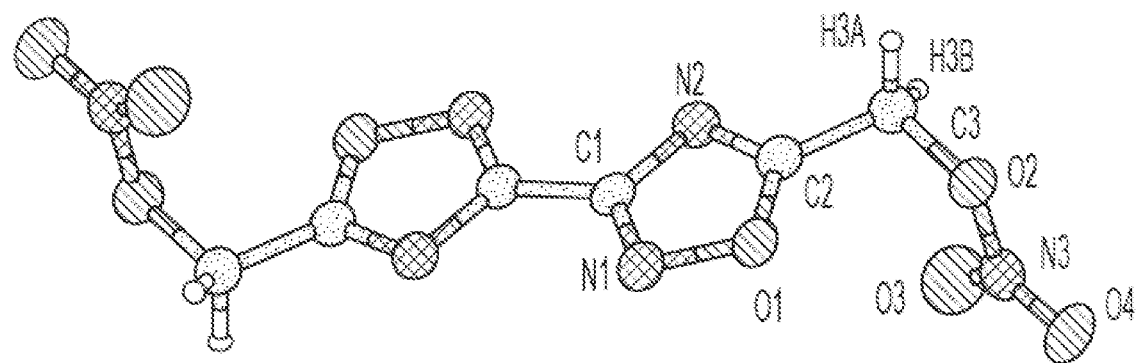
FIG. 13 shows the molecular confirmation of [3,3'-bis(1,2,4-oxadiazole)]-5,5'-diylbis(methylene) dinitrate using X-ray diffractometry, showing the molecular conformation of the compound.
Figure 14:
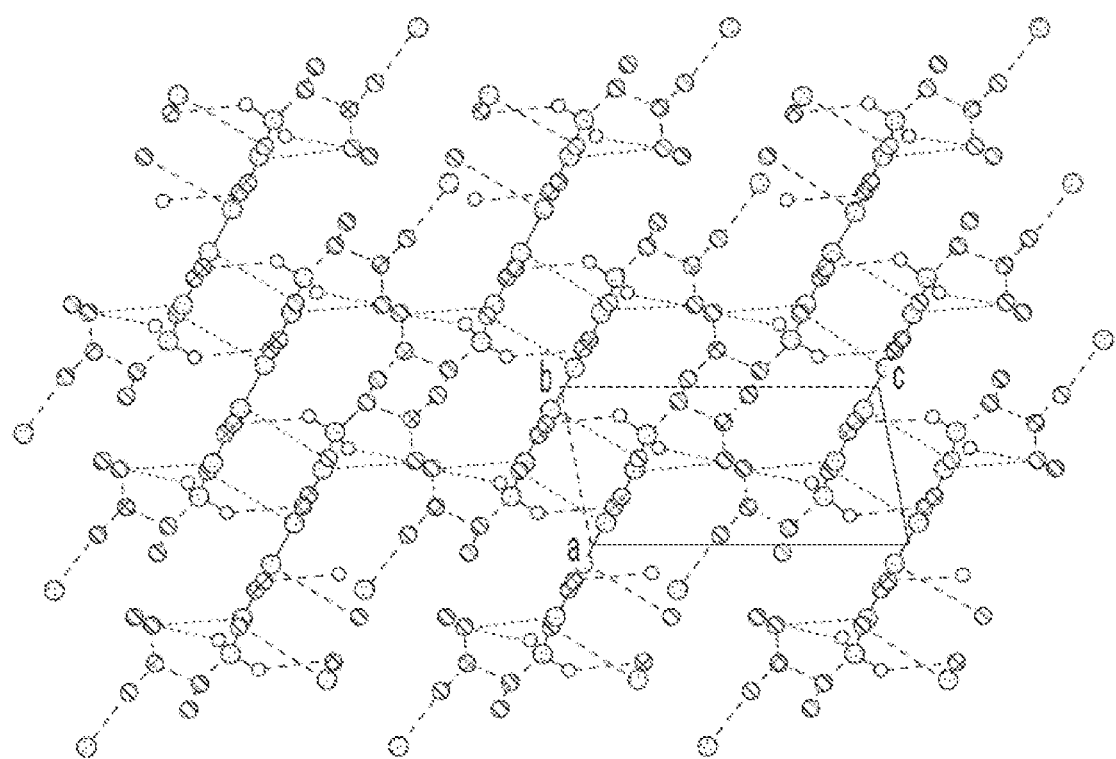
FIG. 14 is an expanded view of a crystal stacking diagram used to examine intermolecular and/or intramolecular interactions between atoms of [3,3'-bis(1,2,4-oxadiazole)]-5,5'-diylbis(methylene) dinitrate.

Single-crystal X-ray diffractometry was used to unequivocally identify [3,3'-Bis(1,2,4-oxadiazole)]-5,5'-diylbis(methylene) dinitrate, confirm its structure, provide an experimentally determined density, and reveal intra- and intermolecular interactions (See FIG. 13). There are no unusual bond lengths or angles. The 1,2,4-oxadiazole rings are planar (root-mean-square deviation=0.0021(2) Å) and the alkyl nitrate groups adopt a trans configuration with respect to the rings. The C3 atom is nearly coplanar with the ring (atom-to-mean plane distance=0.03 Å), whereas the C3-O2 bond is twisted slightly out of the plane, as evidenced by the torsion angles O1-C2-C3-O2=−21.8(3)° and N2-C2-C3-O2=162.8(2)°. The dihedral angle between the oxadiazole ring and the nitrate group is 83.5(1)°. Bifurcated intramolecular contacts between the O3 atoms and the H3B and C2 atoms [O3 . . . H3B=2.360(2) Å; O3 . . . C2=2.856(3) Å] contribute to its stability, whereas van der Waals contacts between the H3A and N2 atoms on adjacent molecules [H3A . . . N2i=2.562(1) Å; symmetry code (i): −x+1, −y, z−2] and between the O3 and O3 atoms on adjacent molecules [O3 . . . O3ii=3.025(1) Å; symmetry code (ii): −x+1, −y+1, −z+1] dominate its intermolecular interactions. In the crystal lattice, the oxadiazoles are arranged face-up in rows [centroid-to-centroid distance=6.028(1) Å, plane-to-plane shift=6.025(2) Å], forming planes parallel to the b axis. The rings are stacked along the a axis with some in close proximity [centroid-to-centroid distance=3.444(2) Å; plane-to-plane shift=1.5542(3) Å] (see FIG. 14).

The diffraction patterns of [3,3'-bis(1,2,4-oxadiazole)]-5,5'-diylbis(methylene) dinitrate are consistent with its being a member the triclinic crystal system (P$\overline{1}$) with one molecule in its unit cell. On the basis of its molecular mass and lattice constants [a=4.8405(4) Å, b=6.0293(4) Å, c=9.4356(7) Å, α=80.399(6)°, β=77.125(7)°, and γ=78.831(6)°], a density of 1.832 g cm$^{-3}$ at 295.9 (1) K is obtained.

In view of the many possible embodiments to which the principles of the disclosed invention may be applied, it should be recognized that the illustrated embodiments are only examples and should not be taken as limiting the scope of the present disclosure. Rather, the scope is defined by the following claims. We therefore claim as our invention all that comes within the scope and spirit of these claims.

We claim:

1. A compound having a structure of Formula I,

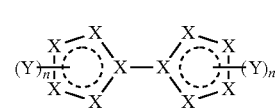

Formula I wherein
each X independently is selected from carbon, CH, nitrogen, NH, or oxygen such that each five-membered ring of Formula I independently is heteroaryl selected from an oxadiazole or an isomer thereof; an oxatriazole or an isomer thereof; or an oxazole having a formula

each Y independently is selected from aliphatic-ONO$_2$ wherein aliphatic is an alkyl group comprising 1 to 5 carbon atoms; and
each n independently is an integer ranging from 1 to 4.

2. The compound of claim 1, wherein each five-membered ring of Formula I is an oxadiazole.

3. The compound of claim 1, wherein the alkyl group is a methylene group.

4. The compound of claim 1, wherein each Y is —CH$_2$ONO$_2$ and each n is 1.

5. The compound of claim 1, having a structure of Formula II or Formula III

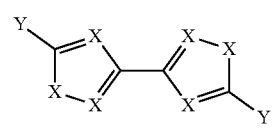

Formula II

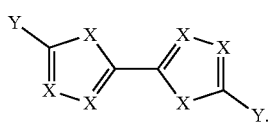

Formula III

6. The compound of claim 5, wherein each Y independently is —CH$_2$ONO$_2$.

7. The compound of claim 1, wherein the compound is

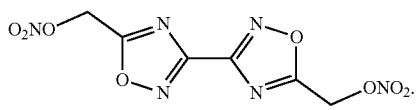

8. The compound of claim 1, wherein the compound has a decomposition temperature ranging from 140° C. to 195° C.

9. The compound of claim 1, wherein the compound has an onset temperature of melting that ranges from greater than 80° C. to 85° C.

10. The compound of claim 1, wherein the compound has an explosive density ranging from greater than 1.75 g/cm$^3$ to 2 g/cm$^3$.

11. The compound of claim 1, wherein the compound has a detonation velocity greater than 8000 m/s to 8200 m/s.

12. A compound selected from

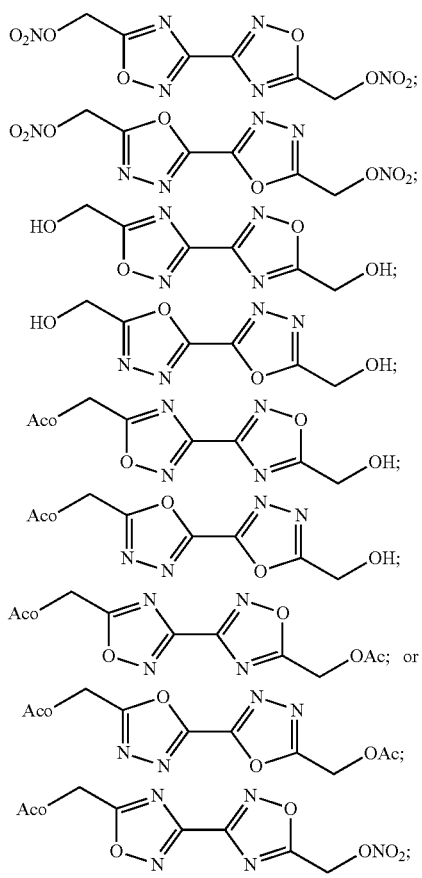

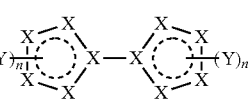

13. A method, comprising using an energetic compound to make a melt-castable explosive composition and/or a propellant plasticizer composition, wherein the energetic compound has a structure of Formula I, Formula I $$(Y)_{\overline{m}}\left[\begin{array}{c}X=X\\X\diagdown X\end{array}\right]X-X\left[\begin{array}{c}X=X\\X\diagdown X\end{array}\right](Y)_n$$

wherein
each X independently is selected from carbon, CH, nitrogen, NH, or oxygen such that each five-membered ring of Formula I independently is heteroaryl selected from an oxadiazole or an isomer thereof; an oxatriazole or an isomer thereof; or an oxazole having a formula

[oxazole structure]

each Y independently is selected from aliphatic-ONO$_2$ wherein aliphatic is an alkyl group comprising 1 to 5 carbon atoms; and
each n independently is an integer ranging from 1 to 4.

* * * * *